(12) United States Patent
Snow et al.

(10) Patent No.: US 8,789,525 B2
(45) Date of Patent: Jul. 29, 2014

(54) TUB FOR HUMIDIFIER

(71) Applicant: ResMed Limited, Bella Vista (AU)

(72) Inventors: John Michael Snow, Killarney Heights (AU); Simon Robert Cork, Wollstonecraft (AU); John Zekic, Quakers Hill (AU); Benjamin John Hunter, Turramurra (AU)

(73) Assignee: ResMed Limited, Bella Vista (AU)

( * ) Notice: Subject to any disclaimer, the term of this patent is extended or adjusted under 35 U.S.C. 154(b) by 0 days.

(21) Appl. No.: 13/733,159

(22) Filed: Jan. 3, 2013

(65) Prior Publication Data

US 2013/0118492 A1     May 16, 2013

Related U.S. Application Data

(63) Continuation of application No. 12/134,310, filed on Jun. 6, 2008, now Pat. No. 8,365,726.

(60) Provisional application No. 60/942,567, filed on Jun. 7, 2007, provisional application No. 61/039,514, filed on Mar. 26, 2008.

(51) Int. Cl.
    *A61M 16/00*     (2006.01)
    *A61M 16/16*     (2006.01)

(52) U.S. Cl.
    CPC .................... *A61M 16/16* (2013.01)
    USPC ................................... 128/203.26

(58) Field of Classification Search
    CPC .............. A61M 2016/1075; A61M 2016/109; A61M 16/161; A61M 16/162; A61M 16/164; A61M 16/165; A61M 16/167; A61M 16/168; A61M 16/1045; Y10S 261/65
    USPC ............ 128/200.24, 200.26, 203.16, 203.17, 128/203.26, 203.27; 261/72.1, 119.1, 261/DIG. 65

See application file for complete search history.

(56) References Cited

U.S. PATENT DOCUMENTS 1,475,289 A     11/1923    Diescher
1,974,843 A      9/1934    Blashfield (Continued)

FOREIGN PATENT DOCUMENTS

AU         200065475 B2     4/2001
DE            275612         1/1913

(Continued)

OTHER PUBLICATIONS

Breas Medical AB "iSleep® 20" Brochure, Dec. 2007 (2 page).

(Continued)

*Primary Examiner* — Lynne Anderson
*Assistant Examiner* — Bradley Philips
(74) *Attorney, Agent, or Firm* — Nixon & Vanderhye, PC

(57) ABSTRACT

A humidifier includes a tub configured to hold a supply of water. The tub includes a tub lid and a tub base adapted to be coupled to the tub lid. The tub further includes a base plate formed of a heat conducting material and adapted to be coupled to the tub base and a seal positioned between the base plate and the tub base. The tub also includes a retaining mechanism with at least one projection that projects from the tub base and is configured to force the base plate against the seal so that the seal is secured against the tub base.

39 Claims, 25 Drawing Sheets

(56) References Cited

U.S. PATENT DOCUMENTS

| | | | |
|---|---|---|---|
| RE19,826 E | 1/1936 | Aisenstein | |
| 2,220,669 A | 11/1940 | Allen | |
| 2,500,404 A | 3/1950 | Donnelly | |
| 2,872,560 A | 2/1959 | Bowles | |
| 2,945,619 A | 7/1960 | Ballard | |
| 2,998,198 A | 8/1961 | Young | |
| 3,090,380 A | 5/1963 | Dold | |
| 3,171,353 A | 3/1965 | McMahan | |
| 3,275,344 A | 9/1966 | Kendt | |
| 3,316,910 A | 5/1967 | Davis | |
| 3,388,705 A | 6/1968 | Grosshandler | |
| 3,584,401 A | 6/1971 | Cryer et al. | |
| 3,612,710 A | 10/1971 | Mount | |
| 3,620,638 A | 11/1971 | Kaye et al. | |
| 3,638,926 A | 2/1972 | Melville et al. | |
| 3,659,604 A | 5/1972 | Melville et al. | |
| 3,690,317 A | 9/1972 | Millman | |
| 3,804,280 A | 4/1974 | van Amerongen et al. | |
| 3,806,102 A | 4/1974 | Valenta et al. | |
| 3,864,440 A | 2/1975 | Giocoechea | |
| 3,954,920 A | 5/1976 | Heath | |
| 4,000,341 A | 12/1976 | Matson | |
| 4,037,994 A | 7/1977 | Bird | |
| 4,049,233 A | 9/1977 | Brandin | |
| 4,051,205 A | 9/1977 | Grant | |
| 4,105,372 A | 8/1978 | Mishina et al. | |
| 4,124,046 A | 11/1978 | Lundberg | |
| 4,152,379 A | 5/1979 | Suhr | |
| 4,164,645 A | 8/1979 | Dogliotti | |
| 4,165,456 A | 8/1979 | Dogliotti | |
| 4,171,190 A | 10/1979 | Hudson | |
| 4,201,737 A | 5/1980 | Carden | |
| 4,203,027 A | 5/1980 | O'Hare et al. | |
| 4,222,971 A | 9/1980 | Eilert | |
| 4,229,142 A | 10/1980 | Le Dall et al. | |
| 4,237,080 A | 12/1980 | Elliott | |
| 4,243,396 A | 1/1981 | Cronenberg | |
| 4,286,815 A | 9/1981 | Clark | |
| 4,336,798 A | 6/1982 | Beran | |
| 4,383,800 A | 5/1983 | Becker et al. | |
| 4,463,248 A * | 7/1984 | Katzman et al. | 392/337 |
| 4,496,132 A | 1/1985 | Winegarten | |
| 4,523,896 A | 6/1985 | Lhenry et al. | |
| 4,532,088 A | 7/1985 | Miller | |
| 4,557,261 A | 12/1985 | Rügheimer | |
| 4,575,128 A | 3/1986 | Sundquist | |
| 4,576,616 A | 3/1986 | Mottram et al. | |
| 4,621,632 A | 11/1986 | Bartels et al. | |
| 4,644,790 A | 2/1987 | Mizoguchi | |
| 4,657,713 A | 4/1987 | Miller | |
| 4,676,237 A | 6/1987 | Wood et al. | |
| 4,686,354 A | 8/1987 | Makin | |
| 4,714,078 A | 12/1987 | Paluch | |
| 4,753,758 A | 6/1988 | Miller | |
| 4,799,287 A | 1/1989 | Belanger | |
| 4,802,819 A | 2/1989 | Bevington | |
| 4,807,616 A | 2/1989 | Adahan | |
| 4,838,258 A | 6/1989 | Dryden et al. | |
| 4,906,417 A | 3/1990 | Gentry | |
| 4,910,384 A * | 3/1990 | Silver | 392/396 |
| 4,913,140 A * | 4/1990 | Orec et al. | 128/203.16 |
| 4,921,642 A | 5/1990 | LaTorraca | |
| 4,926,856 A | 5/1990 | Cambio et al. | |
| 4,941,469 A | 7/1990 | Adahan | |
| 4,943,704 A | 7/1990 | Rabenau et al. | |
| 4,944,310 A | 7/1990 | Sullivan | |
| 4,946,348 A | 8/1990 | Yapp | |
| 4,953,546 A | 9/1990 | Blackmer et al. | |
| 4,953,897 A | 9/1990 | Klober | |
| 4,973,234 A | 11/1990 | Swenson | |
| 4,993,411 A | 2/1991 | Callaway | |
| 5,061,405 A | 10/1991 | Stanek et al. | |
| 5,097,424 A | 3/1992 | Ginevri et al. | |
| 5,127,800 A | 7/1992 | Hyll et al. | |
| 5,199,009 A | 3/1993 | Svast | |
| 5,231,979 A | 8/1993 | Rose et al. | |
| 5,237,987 A | 8/1993 | Anderson et al. | |
| 5,271,391 A | 12/1993 | Graves | |
| 5,329,939 A | 7/1994 | Howe | |
| 5,339,825 A | 8/1994 | McNaughton et al. | |
| 5,349,946 A | 9/1994 | McComb | |
| 5,391,063 A | 2/1995 | Hantle et al. | |
| 5,443,061 A | 8/1995 | Champain et al. | |
| 5,445,143 A | 8/1995 | Sims | |
| 5,474,112 A | 12/1995 | Carola | |
| 5,482,031 A | 1/1996 | Lambert | |
| 5,483,616 A | 1/1996 | Chiu et al. | |
| 5,537,997 A | 7/1996 | Mechlenburg et al. | |
| 5,551,419 A | 9/1996 | Froehlich et al. | |
| 5,558,084 A | 9/1996 | Daniell et al. | |
| 5,564,415 A | 10/1996 | Dobson et al. | |
| 5,577,496 A | 11/1996 | Blackwood et al. | |
| 5,588,423 A * | 12/1996 | Smith | 128/203.26 |
| 5,598,837 A | 2/1997 | Sirianne, Jr. et al. | |
| 5,651,775 A | 7/1997 | Walker et al. | |
| 5,655,522 A | 8/1997 | Mechlenburg et al. | |
| 5,673,687 A | 10/1997 | Dobson et al. | |
| 5,682,289 A | 10/1997 | Schwegler et al. | |
| 5,783,117 A * | 7/1998 | Byassee et al. | 261/29 |
| 5,794,219 A | 8/1998 | Brown | |
| 5,822,715 A | 10/1998 | Worthington et al. | |
| 5,828,943 A | 10/1998 | Brown | |
| 5,832,448 A | 11/1998 | Brown | |
| 5,848,592 A | 12/1998 | Sibley | |
| 5,879,163 A | 3/1999 | Brown et al. | |
| 5,887,133 A | 3/1999 | Brown et al. | |
| 5,888,053 A | 3/1999 | Kobayashi et al. | |
| 5,897,493 A | 4/1999 | Brown | |
| 5,899,855 A | 5/1999 | Brown | |
| 5,913,310 A | 6/1999 | Brown | |
| 5,916,493 A | 6/1999 | Miller et al. | |
| 5,918,603 A | 7/1999 | Brown | |
| 5,933,136 A | 8/1999 | Brown | |
| 5,940,801 A | 8/1999 | Brown | |
| 5,943,473 A * | 8/1999 | Levine | 392/401 |
| 5,951,300 A | 9/1999 | Brown | |
| 5,956,501 A | 9/1999 | Brown | |
| 5,960,403 A | 9/1999 | Brown | |
| 5,985,559 A | 11/1999 | Brown | |
| 5,997,476 A | 12/1999 | Brown | |
| D419,658 S | 1/2000 | Matchett et al. | |
| 6,023,686 A | 2/2000 | Brown | |
| 6,024,694 A | 2/2000 | Goldberg et al. | |
| 6,032,119 A | 2/2000 | Brown et al. | |
| 6,050,260 A | 4/2000 | Daniell et al. | |
| 6,052,511 A | 4/2000 | Birdsell | |
| 6,101,478 A | 8/2000 | Brown | |
| 6,109,865 A | 8/2000 | Ishikawa | |
| 6,129,524 A | 10/2000 | Woollenweber et al. | |
| 6,131,571 A | 10/2000 | Lampotang et al. | |
| 6,135,432 A | 10/2000 | Hebblewhite et al. | |
| 6,144,837 A | 11/2000 | Quy | |
| 6,152,132 A | 11/2000 | Psaros | |
| 6,158,978 A | 12/2000 | Norbury, Jr. | |
| 6,161,095 A | 12/2000 | Brown | |
| 6,186,140 B1 | 2/2001 | Hoague | |
| 6,189,870 B1 | 2/2001 | Withall | |
| 6,202,991 B1 | 3/2001 | Coniglio et al. | |
| 6,210,116 B1 | 4/2001 | Kuczaj et al. | |
| 6,213,119 B1 | 4/2001 | Brydon et al. | |
| 6,216,691 B1 | 4/2001 | Kenyon et al. | |
| 6,216,823 B1 * | 4/2001 | Wilson | 184/106 |
| 6,257,171 B1 | 7/2001 | Rivard | |
| 6,275,652 B1 | 8/2001 | Chauviaux | |
| 6,279,574 B1 | 8/2001 | Richardson et al. | |
| 6,308,706 B1 | 10/2001 | Lammers et al. | |
| 6,314,237 B1 | 11/2001 | Glucksman | |
| 6,332,462 B1 | 12/2001 | Krohn | |
| 6,340,288 B1 | 1/2002 | Hulkkonen et al. | |
| 6,349,724 B1 | 2/2002 | Burton et al. | |
| D454,393 S | 3/2002 | Lynch et al. | |
| 6,397,841 B1 | 6/2002 | Kenyon et al. | |
| 6,398,197 B1 | 6/2002 | Dickinson | |
| 6,435,180 B1 | 8/2002 | Hewson et al. | |

(56) References Cited

U.S. PATENT DOCUMENTS

| | | |
|---|---|---|
| 6,438,180 B1 | 8/2002 | Kavcic et al. |
| 6,471,493 B2 | 10/2002 | Choi et al. |
| D467,335 S | 12/2002 | Lithgow et al. |
| D468,011 S | 12/2002 | Lynch et al. |
| D468,017 S | 12/2002 | McCombs |
| 6,514,053 B2 | 2/2003 | Takura et al. |
| 6,527,309 B1 | 3/2003 | Gaydos et al. |
| 6,543,449 B1 | 4/2003 | Woodring et al. |
| 6,554,260 B1 | 4/2003 | Lipscombe et al. |
| 6,591,834 B1 | 7/2003 | Colla et al. |
| 6,604,390 B1 | 8/2003 | Nooner |
| 6,615,444 B2 | 9/2003 | McGilll et al. |
| 6,622,724 B1 | 9/2003 | Truitt et al. |
| 6,648,664 B1 | 11/2003 | McHugh et al. |
| 6,669,630 B1 | 12/2003 | Joliat et al. |
| 6,672,300 B1 | 1/2004 | Grant |
| D487,311 S | 3/2004 | Lithgow et al. |
| 6,718,973 B2 | 4/2004 | Koch |
| 6,718,974 B1 | 4/2004 | Moberg |
| D493,520 S | 7/2004 | Bertinetti et al. |
| D493,884 S | 8/2004 | Virr et al. |
| 6,772,999 B2 | 8/2004 | Lipscombe et al. |
| 6,775,882 B2 | 8/2004 | Murphy et al. |
| D498,527 S | 11/2004 | Virr et al. |
| 6,811,546 B1 | 11/2004 | Callas et al. |
| 6,827,340 B2 | 12/2004 | Austin et al. |
| 6,837,260 B1 | 1/2005 | Kuehn |
| 6,843,207 B2 | 1/2005 | Kanzaki et al. |
| 6,869,065 B1 * | 3/2005 | Lin .................... 261/3 |
| 6,874,771 B2 | 4/2005 | Birdsell et al. |
| 6,896,478 B2 | 5/2005 | Botros et al. |
| 6,910,483 B2 | 6/2005 | Daly et al. |
| 6,918,389 B2 | 7/2005 | Seakins et al. |
| 6,935,337 B2 | 8/2005 | Virr et al. |
| 6,988,497 B2 | 1/2006 | Levine |
| 7,056,289 B2 | 6/2006 | Kasper et al. |
| 7,089,930 B2 | 8/2006 | Adams et al. |
| 7,096,864 B1 * | 8/2006 | Mayer et al. ............. 128/202.27 |
| 7,111,624 B2 | 9/2006 | Thudor et al. |
| 7,128,729 B2 | 10/2006 | Duchon et al. |
| 7,137,388 B2 | 11/2006 | Virr et al. |
| D542,900 S | 5/2007 | Snow et al. |
| 7,225,809 B1 | 6/2007 | Bowen et al. |
| 7,327,949 B1 | 2/2008 | Cheng et al. |
| 7,364,140 B2 * | 4/2008 | Lipscombe et al. .......... 261/142 |
| 7,413,173 B2 | 8/2008 | DiMatteo et al. |
| 7,478,635 B2 | 1/2009 | Wixey et al. |
| 7,614,398 B2 | 11/2009 | Virr et al. |
| 7,616,871 B2 | 11/2009 | Kramer |
| 7,677,246 B2 | 3/2010 | Kepler et al. |
| 7,938,112 B2 * | 5/2011 | Mayer et al. ............. 128/203.12 |
| 8,006,691 B2 | 8/2011 | Kenyon et al. |
| 8,020,551 B2 | 9/2011 | Virr et al. |
| 8,028,693 B2 | 10/2011 | Trevor-Wilson et al. |
| 8,042,535 B2 | 10/2011 | Kenyon et al. |
| 8,049,143 B2 | 11/2011 | Andel et al. |
| 8,240,306 B2 | 8/2012 | Cortez et al. |
| RE44,453 E | 8/2013 | Virr et al. |
| 2002/0020930 A1 | 2/2002 | Austin et al. |
| 2002/0022973 A1 | 2/2002 | Sun et al. |
| 2002/0056453 A1 | 5/2002 | Klopp et al. |
| 2002/0159897 A1 | 10/2002 | Kegg et al. |
| 2002/0195110 A1 | 12/2002 | Watton |
| 2003/0062045 A1 | 4/2003 | Woodring et al. |
| 2003/0065308 A1 | 4/2003 | Lebel et al. |
| 2003/0066526 A1 | 4/2003 | Thudor et al. |
| 2003/0084900 A1 | 5/2003 | LeClerc et al. |
| 2003/0115085 A1 | 6/2003 | Satoh |
| 2003/0172931 A1 | 9/2003 | Kerechanin, II et al. |
| 2003/0208465 A1 | 11/2003 | Yurko et al. |
| 2003/0230308 A1 | 12/2003 | Linden |
| 2004/0012103 A1 * | 1/2004 | Mulvaney et al. ........... 261/72.1 |
| 2004/0035422 A1 | 2/2004 | Truitt et al. |
| 2004/0055597 A1 * | 3/2004 | Virr et al. ................. 128/203.12 |
| 2004/0065335 A1 | 4/2004 | Huber et al. |
| 2004/0076412 A1 | 4/2004 | Kanzaki et al. |
| 2004/0182047 A1 * | 9/2004 | Thierjung et al. .............. 53/421 |
| 2004/0221843 A1 | 11/2004 | Baecke |
| 2004/0226562 A1 | 11/2004 | Bordewick |
| 2005/0005937 A1 | 1/2005 | Farrugia et al. |
| 2005/0103339 A1 | 5/2005 | Daly et al. |
| 2005/0178383 A1 | 8/2005 | Mackie et al. |
| 2005/0217673 A1 | 10/2005 | Daly et al. |
| 2006/0130836 A1 | 6/2006 | Wixey et al. |
| 2006/0186561 A1 * | 8/2006 | Song et al. ...................... 261/26 |
| 2006/0191531 A1 | 8/2006 | Mayer |
| 2006/0237005 A1 | 10/2006 | Virr et al. |
| 2007/0036662 A1 | 2/2007 | Pensola et al. |
| 2007/0134085 A1 | 6/2007 | Daly et al. |
| 2007/0210462 A1 | 9/2007 | Felty et al. |
| 2008/0072900 A1 | 3/2008 | Kenyon et al. |
| 2008/0105257 A1 | 5/2008 | Klasek et al. |
| 2008/0302361 A1 | 12/2008 | Snow et al. |
| 2009/0120434 A1 | 5/2009 | Smith et al. |
| 2009/0229606 A1 | 9/2009 | Tang et al. |
| 2010/0154796 A1 | 6/2010 | Smith et al. |
| 2010/0192094 A1 | 7/2010 | Jeha et al. |
| 2010/0229867 A1 | 9/2010 | Bertinetti et al. |
| 2011/0073109 A1 * | 3/2011 | Mayer et al. ............. 128/203.26 |
| 2011/0239426 A1 * | 10/2011 | Denslow ........................ 29/271 |
| 2011/0271956 A2 | 11/2011 | Smith et al. |
| 2012/0319313 A1 * | 12/2012 | Davis ........................ 261/119.1 |

FOREIGN PATENT DOCUMENTS

| | | |
|---|---|---|
| DE | 30 05 094 A1 | 8/1981 |
| DE | 36 42 637 A1 | 6/1988 |
| DE | 38 23 242 A1 | 2/1990 |
| DE | 90 14 848 A1 | 3/1991 |
| DE | 41 38 098 C2 | 11/1991 |
| DE | 42 44 493 A1 | 7/1993 |
| DE | 93 17 450 U1 | 6/1994 |
| DE | 36 23 162 A1 | 7/1994 |
| DE | 37 89 221 T2 | 8/1994 |
| DE | 94 09 231 U1 | 12/1994 |
| DE | 195 15 739 A1 | 11/1996 |
| DE | 196 30 466 A1 | 2/1998 |
| DE | 298 17 685 U1 | 10/1998 |
| DE | 694 09 024 T2 | 10/1998 |
| DE | 197 52 672 C1 | 3/1999 |
| DE | 299 09 611 U1 | 10/1999 |
| DE | 100 16 005 A1 | 12/2001 |
| DE | 202 13 232 U1 | 4/2003 |
| DE | 102005007773 A1 | 9/2005 |
| EP | 0 201 985 A1 | 11/1986 |
| EP | 0 274 996 A2 | 7/1988 |
| EP | 0339 234 A1 | 11/1989 |
| EP | 0 376 584 A2 | 7/1990 |
| EP | 0 589 429 B1 | 3/1994 |
| EP | 0 845 277 A2 | 6/1998 |
| EP | 0 893 750 A2 | 1/1999 |
| EP | 0 903 160 A1 | 3/1999 |
| EP | 1 023 912 A2 | 8/2000 |
| EP | 1 055 431 A2 | 11/2000 |
| EP | 1 087 322 A2 | 3/2001 |
| EP | 1 138 341 A2 | 10/2001 |
| EP | 1 318 307 A1 | 6/2003 |
| EP | 1 374 938 A1 | 1/2004 |
| FR | 2 323 436 A1 | 4/1977 |
| FR | 2 663 547 A1 | 12/1991 |
| FR | 2 714 985 A1 | 7/1995 |
| GB | 1556492 A | 11/1979 |
| GB | 2069607 A | 8/1981 |
| GB | 2 116 434 | 9/1983 |
| GB | 2 173 107 | 10/1986 |
| GB | 2 173 108 | 10/1986 |
| GB | 2 177 006 A | 1/1987 |
| GB | 2 192 136 A | 1/1988 |
| GB | 2 293 325 A | 3/1996 |
| GB | 2 353 904 A | 3/2001 |
| JP | 55-104925 A | 1/1979 |

(56) References Cited

FOREIGN PATENT DOCUMENTS

| | | |
|---|---|---|
| JP | 58-36560 A | 3/1983 |
| JP | 02-19168 A | 1/1990 |
| JP | 05-104681 A | 4/1993 |
| JP | 06-190928 A | 7/1994 |
| JP | 07-145795 A | 6/1995 |
| JP | 07-37195 U | 7/1995 |
| JP | 08-178781 A | 7/1996 |
| JP | 09-103490 A | 4/1997 |
| JP | 11-398 A | 1/1999 |
| JP | 2000-237316 A | 9/2000 |
| JP | 2000-337670 A | 12/2000 |
| JP | 2001-160102 A | 6/2001 |
| JP | 2002-206498 A | 7/2002 |
| JP | 2002-248167 A | 9/2002 |
| JP | 2002-253672 A | 9/2002 |
| JP | 2002-306601 A | 10/2002 |
| JP | 2004-057278 A | 2/2004 |
| JP | 2004-532666 A | 10/2004 |
| WO | WO 93/05451 A1 | 3/1993 |
| WO | WO 95/15778 A1 | 6/1995 |
| WO | WO 97/32619 A1 | 9/1997 |
| WO | WO 98/31937 A1 | 7/1998 |
| WO | WO 98/33433 A1 | 8/1998 |
| WO | WO 98/57691 A1 | 12/1998 |
| WO | WO 99/13932 A1 | 3/1999 |
| WO | WO 99/22793 A1 | 5/1999 |
| WO | WO 99/22794 A1 | 5/1999 |
| WO | WO 99/64747 A1 | 12/1999 |
| WO | WO 00/21602 A1 | 4/2000 |
| WO | WO 00/27457 A1 | 5/2000 |
| WO | WO 00/32261 A1 | 6/2000 |
| WO | WO 00/38771 A1 | 7/2000 |
| WO | WO 00/42324 A2 | 7/2000 |
| WO | WO 01/10489 A2 | 2/2001 |
| WO | WO 01/32069 A2 | 5/2001 |
| WO | WO 01/73653 A1 | 10/2001 |
| WO | WO 02/02169 A1 | 1/2002 |
| WO | WO 02/13898 A2 | 2/2002 |
| WO | WO 02/066107 A1 | 8/2002 |
| WO | WO 03/099367 A2 | 12/2003 |
| WO | WO 2004/043528 A1 | 5/2004 |
| WO | WO 2004/112873 A | 12/2004 |
| WO | WO 2004112873 A1 * | 12/2004 ............ A61M 16/16 |
| WO | WO 2006/012877 A1 | 2/2006 |
| WO | WO 2007/019628 A1 | 2/2007 |
| WO | WO 2008/056993 A2 | 5/2008 |
| WO | WO 2009/059359 A1 | 5/2009 |
| WO | WO 2009/156921 A1 | 12/2009 |
| WO | WO 2010/092496 A1 | 8/2010 |

OTHER PUBLICATIONS

De Vilbiss® Healthcare, "DeVilbiss IntelliPAP® Standard CPAP System," Nov. 2007 (2 pages).
Fisher & Paykel Healthcare "SleepStyle™ 200 CPAP Series" Specification Sheet, 1998 (4 pages).
Fisher & Paykel Healthcare "SleepStyle™ 600 CPAP Series" Specification Sheet, 2005 (4 pages).
Fisher & Paykel Healthcare Two Easy Steps to Comfort, Humidification and Nasal CPAP Therapy, Aug. 1995 (4 pages).
German Patient Manual for Hoffrichter/Sandmann CPAP Respirator—Perfect CPAP Therapy, Mar. 1998 (30 pages plus Translation Verification Certificate).
Hoffrichter "Vector CPAP—Therapy With Technical Mastery", Oct. 1998 (4 pages).
Hoffrichter "Vector therapy in perfection" Brochure, 2002 (2 pages).
J. H. Emerson Co., Cough Assist, "Non-Invasive Removal of Bronchial Secretions," (2 pages), 2002.
Madaus Schwarzer Medizinetechnik, "New Approaches in Diagnosis and Therapy—Max nCPAP User Manual", Mar. 1994 (38 pages).
Madaus Schwarzer Medizintechnik, "New Approaches in Diagnosis and Therapy—Moritz biLevel User Manual", May 1994 (38 pages).
MAP Medizintechnik fuer Arzt and Patient "max II nCPAP moritz II biLevel—The gentle therapy for sleep-related breathing disorders" Brochure, 2000 (4 pages).
MAP Medizintechnik, "minni Max nCPAP®" brochure, Mar. 2005 (12 pages).
MAP Medizintechnik, "Moritz II biLEVEL®—The gentle therapy for sleep-related breathing disorders" brochure, Jan. 2001 (6 pages).
MAP Medizin-Technologie GmbH "minni Max nCPAP®, The respiratory therapy device with•out an integrated humidifier", Dec. 2003 (17 pages).
MAP Medizin-Technologie GmbH, Moritz® S/Moritz® ST—Sailing toward therapeutic success . . . , Jul. 2004 (4 pages).
Photos of HumidAire™ (11 pages), 2001.
Photos of MAP Humidifier and Tub, undated (2 pages and cover sheet), 2002.
Photos of tray system available before the critical date, with sample flow generator and humidifier (5 pages), 2002.
ResMed, "Sullivan® HumidAire® User's Instructions", 1998 (8 pages).
ResMed, "The Sullivan® HumidAire™", 1997 (1 page).
Respironics "System One Heated Humidifier User Manual", May 2009 (20 pages).
U.S. Appl. No. 13/944,960—Virr et al., filed Jul. 18, 2013.
U.S. Appl. No. 60/707,949, filed Aug. 15, 2005 (p. 6 of specification).
U.S. Appl. No. 60/707,951, filed Aug. 15, 2005 (p. 6 of specification).

* cited by examiner

TUB FOR HUMIDIFIER

CROSS REFERENCE TO RELATED APPLICATION

This application is a continuation of U.S. Ser. No. 12/134,310, filed Jun. 6, 2008, now U.S. Pat. No. 8,365,726, which claims priority to U.S. Applications 60/942,567, filed Jun. 7, 2007, and 61/039,514, filed Mar. 26, 2008, each of which is incorporated herein by reference in its entirety.

FIELD OF THE INVENTION

The present invention relates to a tub for a humidifier. The present invention also relates to a humidifier for a breathable gas supply apparatus, and particularly but not exclusively, to such apparatus for use in Continuous Positive Airway Pressure (CPAP) treatment of conditions such as Obstructive Sleep Apnea (OSA) and other respiratory disorders and diseases such as emphysema. Although the present invention is described herein in its application to CPAP treatment apparatus, it should be appreciated that the features of the present invention will have application to other fields of application, such as a mechanical ventilation and assisted respiration.

BACKGROUND OF THE INVENTION

CPAP treatment of OSA, a form of Noninvasive Positive Pressure Ventilation (NIPPV), involves the delivery of a pressurized breathable gas, usually air, to a patient's airways using a conduit and a patient interface, for example, a mask. Gas pressure employed for a CPAP typically range from 4 cm $H_2O$ to 28 cm $H_2O$, at flow rates of up to 180 L/min (measured at the patient interface), depending on patient requirements. The pressurized gas acts as a pneumatic splint for the patient's airway, preventing airway collapse, especially during the inspiratory phase of respiration.

CPAP machines including an airflow generator for supplying pressurized air to the patient are known, and over recent years there has been commercial incentive for more compact CPAP machines. However, in seeking to reduce the size of the CPAP machines there has been a trade-off between reduced size on the one hand and reduced performance on the other.

The advantages of incorporating humidification of the air supply to a patient are known, and CPAP machines are known which incorporate humidifying devices, either separately from the flow generator or integrated therewith. An example of an integrated flow generator/humidifier is the ResMed S7 sold by the assignee of the present application. An example of a humidifier which is separately provided to be connectable to a flow generator is disclosed in U.S. Patent Application Publication 2008/0072900 A1, the entire contents of which are incorporated herein by reference.

It is known to provide a heating unit, such as a heating plate, to a humidifier to increase the amount of water vapor in the flow of breathable gas. Reducing the size of CPAP machines, including humidifiers, has led to a decrease in the size of water containers making it more difficult to provide humidification of the air supply during the entirety of the patient's sleep cycle. The reduction in the size of humidifier tubs results in a decrease in the surface area of the water exposed to the flow of air provided by the flow generator. This creates problems in maintaining a sufficient moisture pickup by the airflow passing through the tub and requires that the flow generator motor run faster, which produces more noise.

The integration of humidifiers with flow generators also makes it more difficult to clean the water container of the humidifier.

SUMMARY OF THE INVENTION

One aspect of the invention relates to a humidifier tub that provides enhanced heating for use with a CPAP device.

Another aspect of the invention relates to a humidifier tub that provides increased usable water capacity for use with a CPAP device.

Still another aspect of the invention relates to a humidifier tub for use with a CPAP device that includes a removable base plate to permit cleaning.

According to an embodiment of the invention, a humidifier comprises a tub. The tub comprises a base plate; a tub base; a seal between the base plate and the tub base; and a latch mechanism that connects the base plate to the tub base so that the base plate is engaged with the seal.

According to another embodiment of the present invention, the humidifier comprises a tub lid configured to cover the tub base. The tub and the tub lid form a water container.

According to still another embodiment of the present invention, the humidifier comprises a cradle configured to receive the water container.

According to yet another embodiment of the invention, the cradle is configured to be connected to a flow generator that supplies an air flow to the water container.

According to a further embodiment of the invention, the cradle comprises a hinged lid that is pivotable between an open position permitting insertion of the water container into the cradle and a closed position covering the inserted water container.

According to an even further embodiment, the hinged lid comprises an air outlet pipe configured to communicate with an outlet of the tub lid when the lid is the closed position.

According to another embodiment of the invention, the cradle comprises a heating element configured to contact the base plate when the water container is inserted into the cradle.

According to another embodiment, a CPAP device includes a humidifier according to the invention.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings.

DETAILED DESCRIPTION OF ILLUSTRATED EMBODIMENTS

The following description is provided in relation to several embodiments which may share common characteristics and features. It is to be understood that one or more features of any one embodiment may be combinable with one or more features of the other embodiments. In addition, any single feature or combination of features in any of the embodiments may constitute additional embodiments.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The term "air" will be taken to include breathable gases, for example air with supplemental oxygen. It is also acknowledged that the blowers described herein may be designed to pump fluids other than air.

1.0 Humidifier

Figure 1:
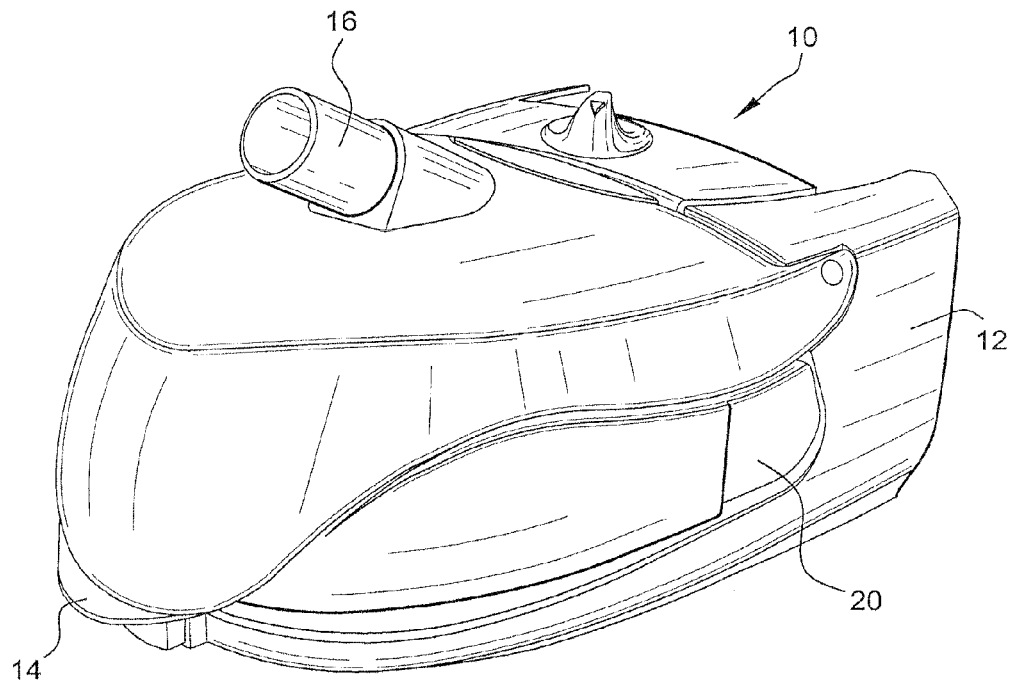
FIG. 1 schematically illustrates a humidifier according to one sample embodiment of the present invention.

Referring to FIG. 1, a humidifier 10 according to an embodiment of the present invention includes a humidifier control base or cradle 12 and a lid 14 hinged to the cradle 12. The hinged lid 14 includes an air outlet pipe 16 which is configured for connection to a hose to deliver a supply of pressurized, breathable gas to a patient via a patient interface, such as a mask. The humidifier 10 includes a water container 20 which is configured to store a supply of water used to humidify the supply of breathable gas. The water container 20 is configured to be inserted, or "dropped," into the cradle 12. The hinged lid 14 is pivotable to an open position (not shown) for insertion of the water container 20 and pivotable to the closed position shown in FIG. 1 to secure the water container 20 in an operable position for connection of the humidifier 10 to a flow generator (not shown). The cradle 12 facilitates the correct assembly of the humidifier 10 with a flow generator. The cradle 12 may include a heating element or plate to heat water within the container 20. Upon insertion of the water container 20 into the cradle 12, the heating element contacts a base plate of the water container 20.

When operating with a hose attached, the lid 14 may be snapped down to create an airtight path, for example using a seal or seals. When the humidifier needs refilling, cleaning, and/or maintenance, the lid may be raised, with the hose still attached, so that the water container is easily accessible. The seal, or seals, of the lid 14 also forms a part of a spill back protection and spitting requirements that protect both the patient and a flow generator. The humidifier is designed to work in a hot and/or humid environment and may be formed of a material that is durable and safe for the patient.

The humidifier is configured to be connected to a flow generator. For example, the humidifier may be connected to a flow generator in a manner similar to that disclosed in WO 2004/112873 A1, the entire contents of which are incorporated by reference herein.

2.0 Tub First Embodiment

Figure 2:
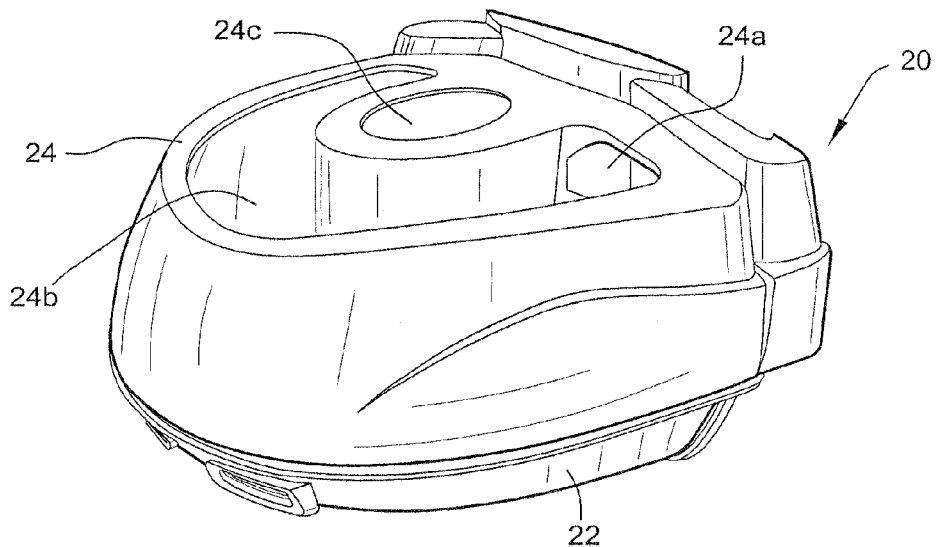
FIG. 2 schematically illustrates a water container of the humidifier of FIG. 1.

As shown in FIG. 2, the water container 20 includes a tub 22 and a tub lid 24. The tub lid 24 includes an air inlet aperture 24a that communicates with an air outlet aperture of the flow generator when the humidifier 10 is connected to the flow generator. The tub lid 24 also includes a U-shaped air passage 24b and a humidified air outlet 24c. The humidified air outlet 24c communicates with the air outlet pipe 16 when the hinged lid 14 is in the position shown in FIG. 1 to deliver humidified air to the delivery hose.

Figure 3A:
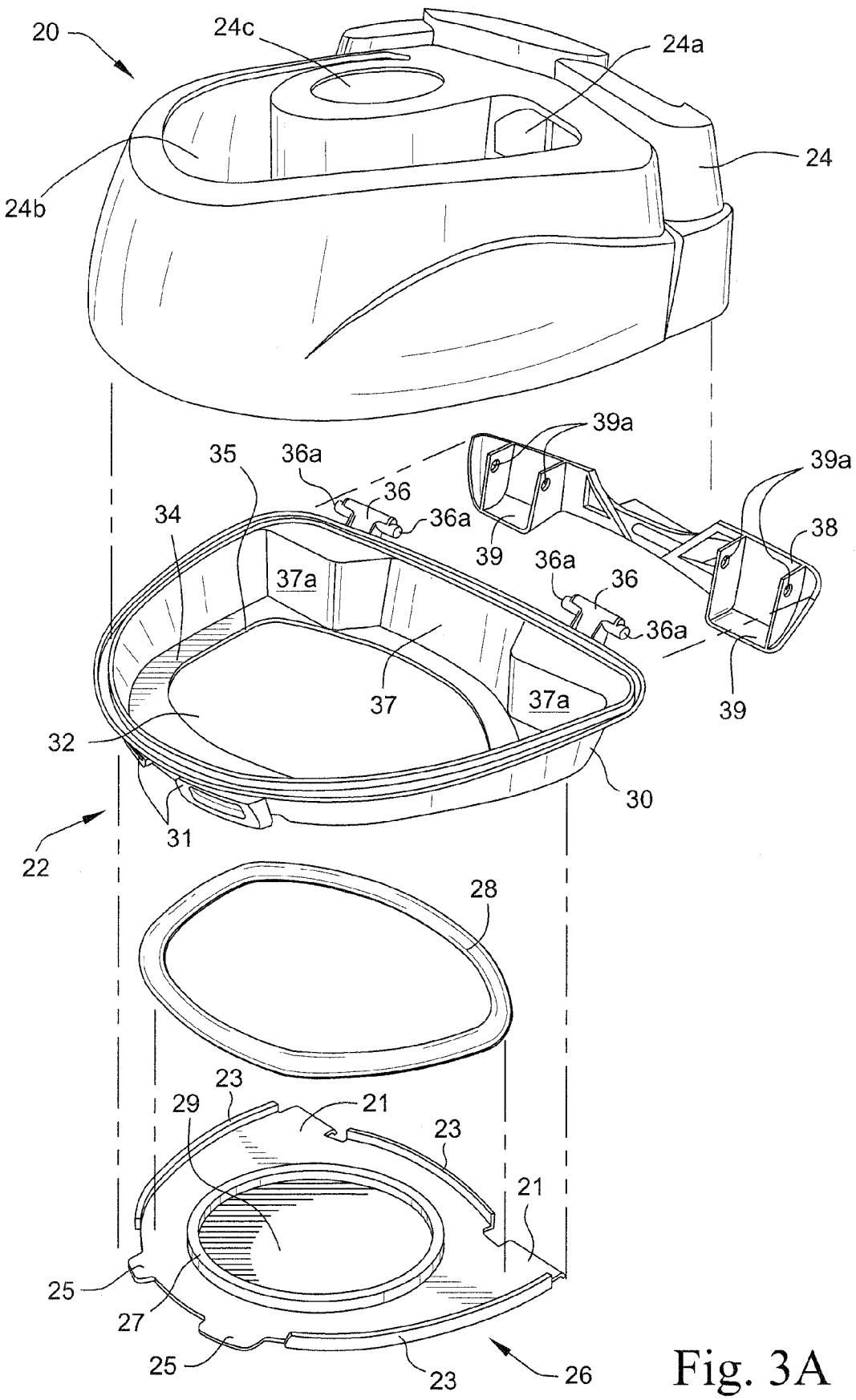
FIG. 3A schematically illustrates an exploded assembly view of the cleanable water container of FIG. 2.

Referring to FIG. 3A, the tub 22 includes a base plate 26 and a tub base 30. The base plate 26 may be formed by stamping, for example, a stainless steel plate. A stamped ring 27 may be formed on the base plate 26 to provide structural rigidity to the base plate 26 so as to provide a flat surface 29. The base plate 26 is also formed with alignment tabs 25 and latch tabs 21.

A face seal 28 is provided between the base plate 26 and the tub base 30. The base plate 26 is attached to the tub base 30, with the face seal 28 therebetween, by inserting the alignment tabs 25 into alignment slots 31 formed in the tub base 30. The portion of the tub base 30 defining the alignment slots 31 may act as feet for the tub 22 to keep the tub 20 level when filling. The alignment slots 31 may be spaced, for example, about 5 mm-15 mm apart, for example about 10 mm. The alignment slots 31 are asymmetrical to ensure correct placement of the base plate 26.

An overcenter latch 38 is connected to the tub base 30 by pivot hinges 36 (FIG. 3D) and the tub 22 is sealed by pivoting the overcenter latch 38 so that latches 39 catch to engage the latch tabs 21 of the base plate 26 to provide a substantially waterproof sealed connection between the tube base 30 and the base plate 26. The latches 39 catch to engage the latch tabs 21 when the overcenter latch 38 is in the engaged position (see FIG. 4) to bias the base plate 26 towards the tub base 30. The face seal 28 is compressed between the base plate 26 and the tub base 30 by the overcenter latch 38 to provide the substantially waterproof seal. As shown in FIG. 4, the overcenter latch 38 may include a textured surface 37 to improve a user's grip on the overcenter latch 38 to permit the overcenter latch 38 to be moved between the engaged and disengaged positions.

The tub base 30 includes a bottom peripheral edge 34 which includes a rim 35 that defines an opening 32 in the tub base 30. The face seal 28 has a shape generally corresponding to the bottom peripheral edge 34 of the tub base 30 and the face seal 28 has a width that is sufficient to permit some misalignment between the tub base 30 and the base plate 26 while still maintaining the substantially waterproof seal. The bottom peripheral edge 34 serves to conceal the edges of the base plate 26, loosely retain the seal 28 during connection of the tub base 30 to the base plate 26, and protect the seal 28 from the edges of the base plate 26 during the connection.

When assembled, the connection of the latch catches 39 and the latch tabs 21 and the insertion of the alignment tabs 25 into the alignment slots 31 define a generally triangular compression region for the face seal 28, which may be, for example, an O-ring. As shown in FIG. 3A, the seal 28 may have a generally D-shaped configuration. It should be appreciated, however, that the seal 28 may have another shape, for example an oval shape.

Figure 3B:
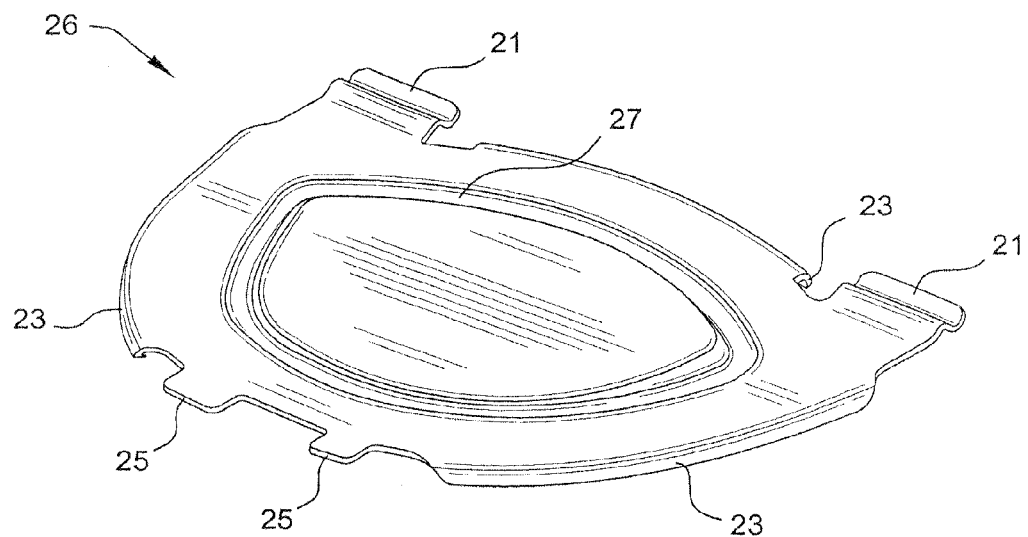
FIG. 3B schematically illustrate a bottom perspective view of a variant of a base plate usable in the assembly of FIG. 3A.

The base plate 26 may also comprise raised edges 23 between the latch tabs 21 and between the latch tabs 21 and the alignment tabs 25. The raised edges 23 add stiffness to the base plate 26 to permit the base plate 26 to resist bending under the stresses induced by the pressure of compressing the seal 28. The stamped ring 27 acts to isolate the contact surface of the base plate 26 from the installation forces and enable the seal pressing process to maintain a flat region. In a variant shown in FIG. 3B, the stamped ring 27 may be formed to match the shape of the seal 28.

The tub base 30 may include one or more ribs 37a provided around a portion of the perimeter of the opening 32 to stiffen the portion of the tub base 30 that will experience high connection forces. The rear portion of the tub base 30 will experience high connection forces when the overcenter latch 38 is connected to the latch tabs 21. The rear corners of the tub base 30 will experience the highest connection forces as the latch catches 39 are connected to the tub base 30 at these locations. The rib 37a act to prevent deflection of the rear portion of the tub base 30. A central gap 37 may be provided in the rib 37a to enable water to drain onto the base plate 26 and ensure that all of the water in the tub 22 is usable.

Figure 3C:
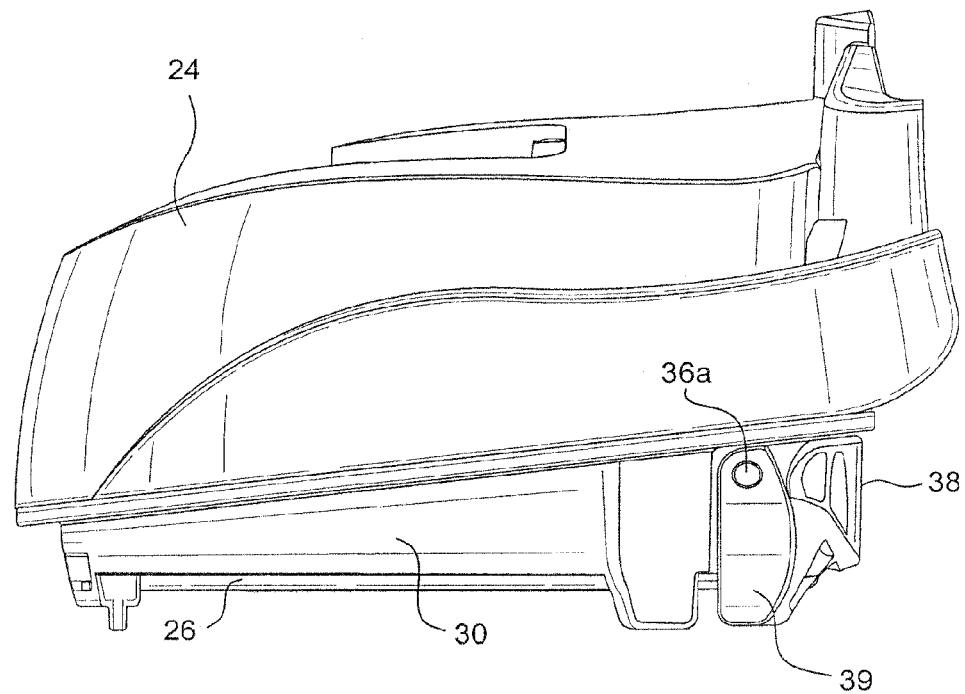
FIG. 3C schematically illustrates a side elevation view of the cleanable water container of the humidifier of FIG. 1.
Figure 3D:
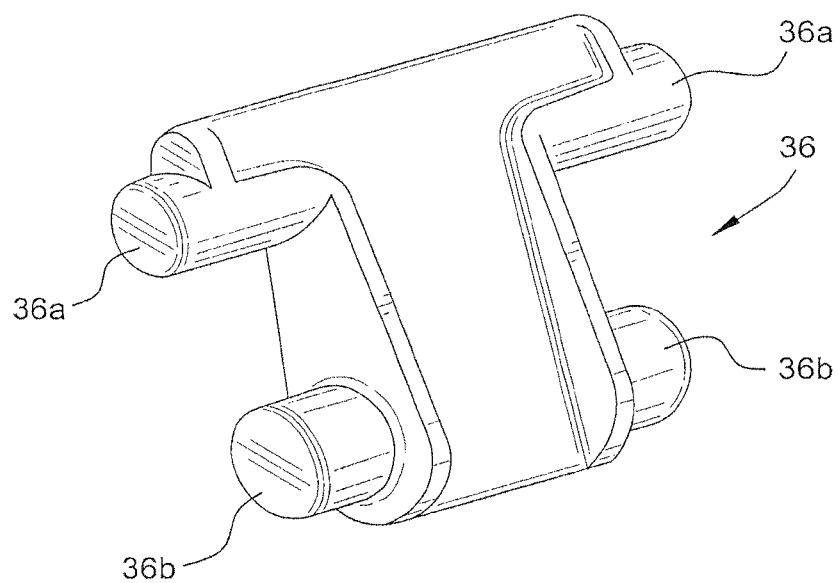
FIG. 3D schematically illustrates a pivot hinge usable with the water container of FIGS. 3A-3C.
Figure 4:
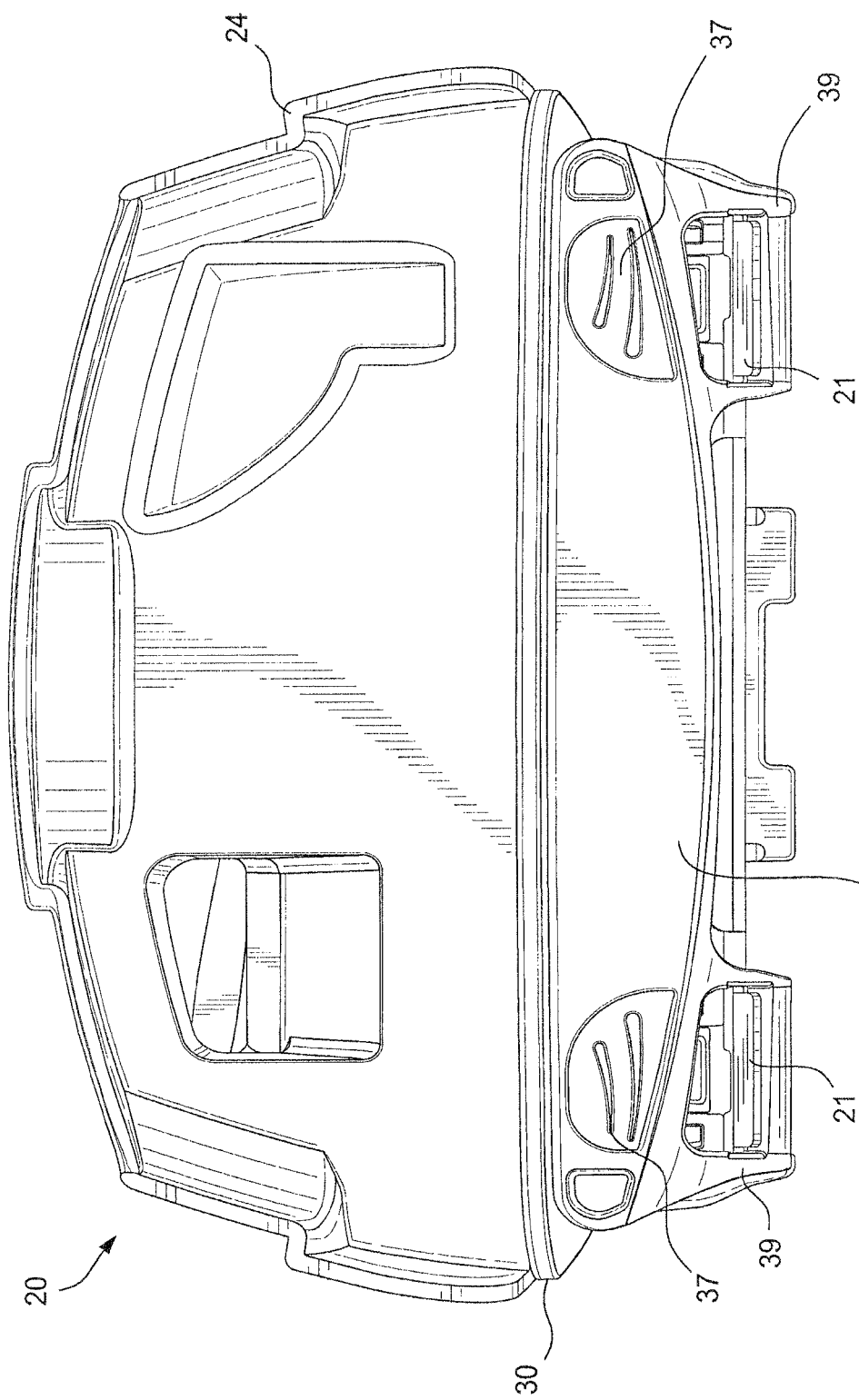
FIG. 4 schematically illustrates a rear elevation view of the cleanable water container of FIGS. 2 and 3A-3D.

Referring to FIGS. 3C and 3D, the pivot hinges 36 are secured to the tub base 30 by pivots 36b of the pivot hinge 36. The rear of the tub base 30 may include four protrusions having holes in each protrusion to accept the pivots 36b of the pivot hinges 36. The latch catches 39 include holes or apertures 39a (FIG. 3A) configured to receive respective pivots 36a of the pivot hinge 36.

The overcenter latch 38 forms a part of the user interface for the humidifier tub. The overcenter latch 38 provides the interfaces for opening and closing the overcenter latch 38 and it interfaces with the base plate 26 to produce the compression force on the face seal 28.

2.1 Tub Second Embodiment

Figure 5:
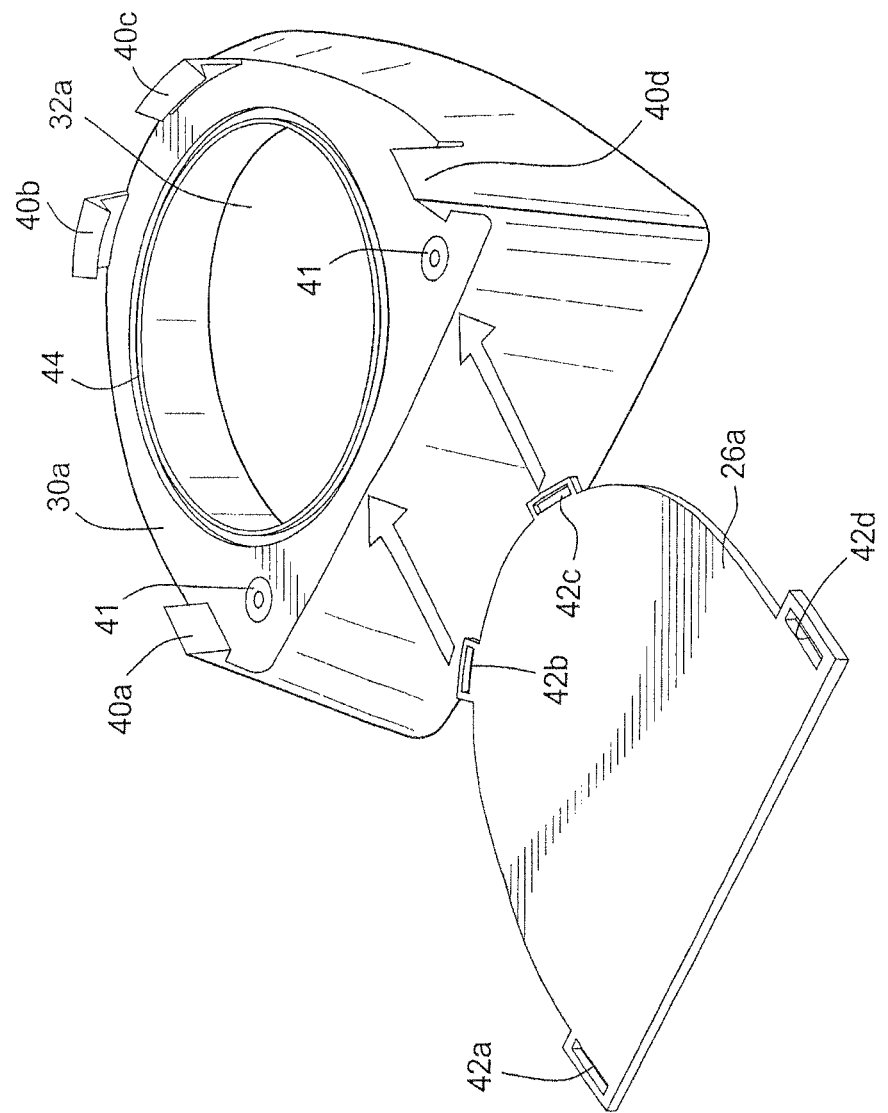
FIGS. 5 and 6 schematically illustrate a humidifier tub according to another sample embodiment of the present invention.
Figure 6:
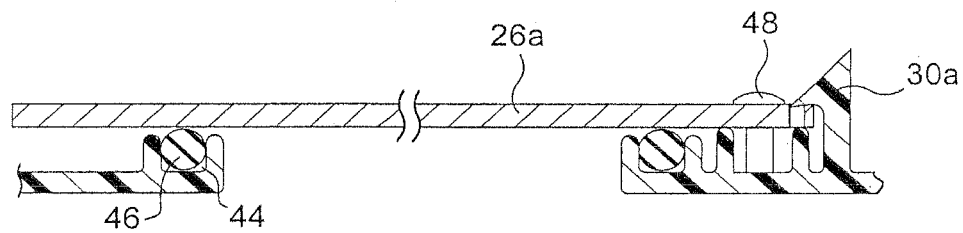

Referring to FIGS. 5 and 6, according to another embodiment of the present invention, the tub base 30a may include a plurality of locking tabs 40a-40d. The base plate 26a is inserted over the opening 32a in the tub base 30a as shown by the arrows in FIG. 5. It should also be appreciated that the base plate 26a may be inserted over the opening in a direction perpendicular to the direction shown by the arrows. The locking tabs 40a-40d are resilient and are received in locking slots 42a-42d provided in the base plate 26a in a snap-in manner. A groove 44 surrounds the periphery of the opening 32a in the tub base for receipt of a seal 46, such as an O-ring. The tub base 30a may also include fastener fittings 41 for receipt of fasteners 48. It should be appreciated that the fasteners 48 may be any releasable fastener.

2.2 Tub Third Embodiment

Figure 7:
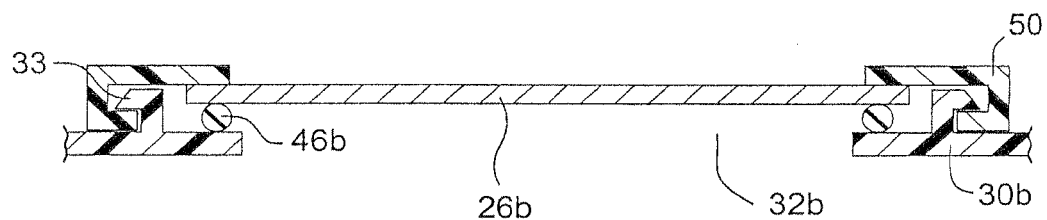
FIG. 7 schematically illustrates a humidifier tub according to another sample embodiment of the invention.

Referring to FIG. 7, the base plate 26b may be releasably secured to the tub base 30b by tabs 33 formed on the tub base 30b and snap rings 50. The base plate 26b is placed over the opening 32b in the tub base 30b in contact with the seal 46b. The snap rings 50 are then placed over the base plate 26b and in engagement with the tabs 33 to secure the base plate 26b between the snap rings 50 and the seal 46b. The tabs 33 are resiliently deformed by insertion of the snap rings 50 so that the snap rings 50 are secured in the position shown in FIG. 7.

2.3 Tub Fourth Embodiment

Figure 8:
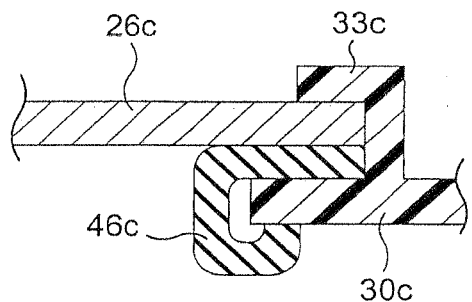
FIG. 8 schematically illustrates a humidifier tub according to another sample embodiment of the present invention.

According to another embodiment shown in FIG. 8, the base plate 26c may be secured to the tub base 30c by tabs 33c and a seal 46c. The seal 46c may be secured to the tub base 30c so as to secure the base plate 26c between the seal 46c and the tabs 33c.

2.4 Tub Fifth Embodiment

Figure 9:
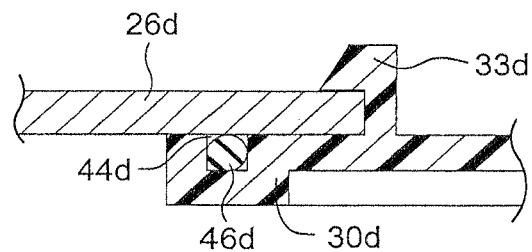
FIG. 9 schematically illustrates a humidifier tub according to another sample embodiment of the present invention.

According to another embodiment shown in FIG. 9, the base plate 26d may be secured to the tub base 30d by tabs 33d. A groove 44d is provided in the tub base 30d and the seal (e.g., O-ring) 46d is provided in the groove 44d to seal the connection between the base plate 26d and the tub base 30d.

2.5 Tub Sixth Embodiment

Figure 10:
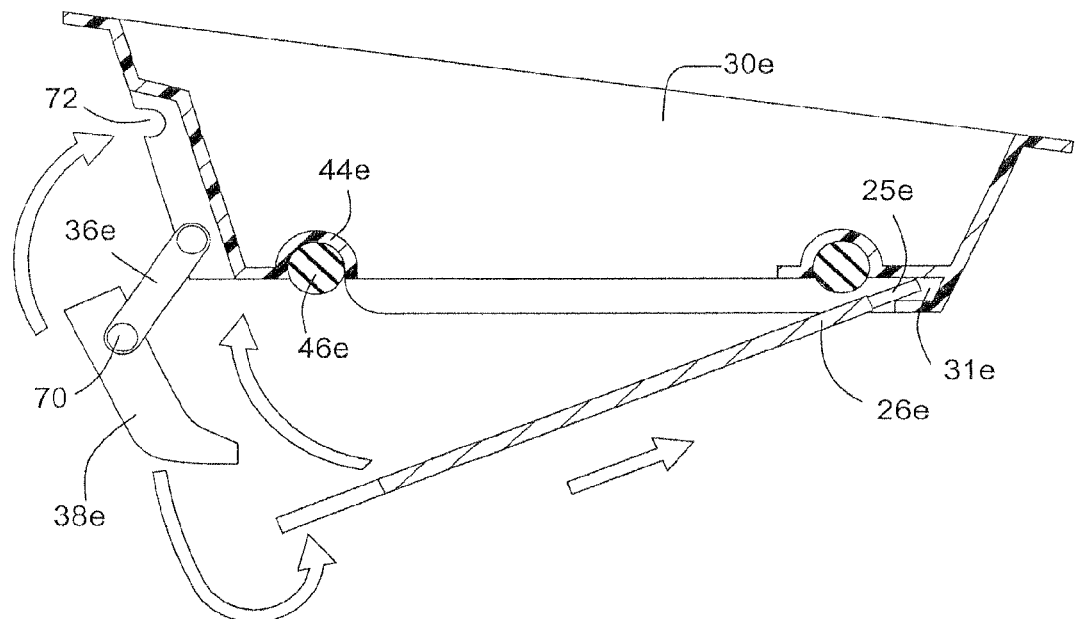
FIG. 10 schematically illustrates a humidifier tub according to another sample embodiment of the present invention.

Referring to FIG. 10, the tub base 30e includes a groove 44e to accommodate a seal 46e, such as an O-ring. Alignment tabs 25e of the base plate 26e are inserted into alignment slots 31e in the tub base 30e and the opposite end of the base plate 26e is then pivoted toward the tub base 30e. An overcenter latch 38e connected to the tub base 30e by a pivot hinge 36e. After the alignment tabs 25e of the base plate 26e are inserted into the alignment slots 31e, the opposite end of the base plate 26e is pivoted toward the tub base 30e. A first end of the overcenter latch 38e is pivoted into engagement with opposite end of the base plate 26e and the second end of the overcenter latch 38e is then pivoted into the assembled condition such that a pin 70 of the pivot hinge 36e is placed in a notch 72 in the tub base 30e.

2.6 Tub Seventh Embodiment

Figure 11:
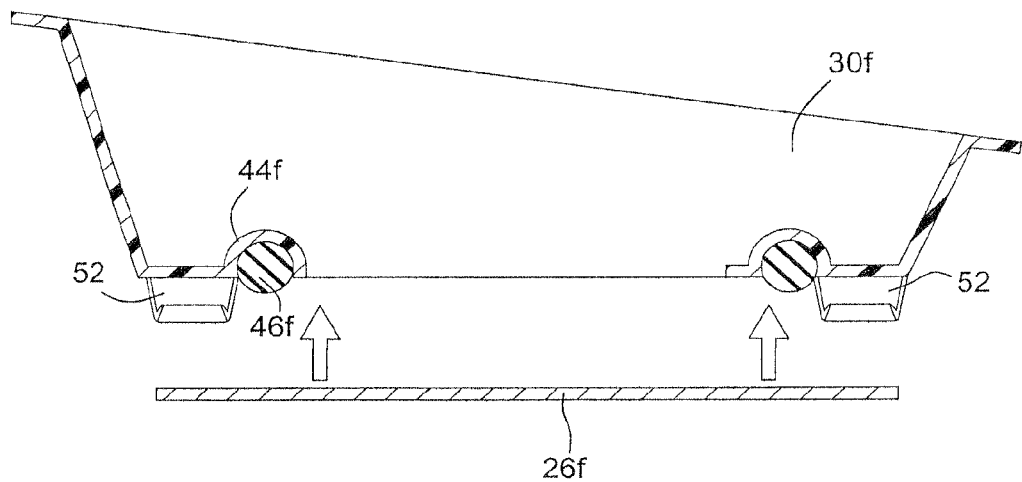
FIGS. 11 and 12 schematically illustrate a humidifier tub according to another sample embodiment of the present invention and FIG. 12A illustrates an additional variant.
Figure 12:
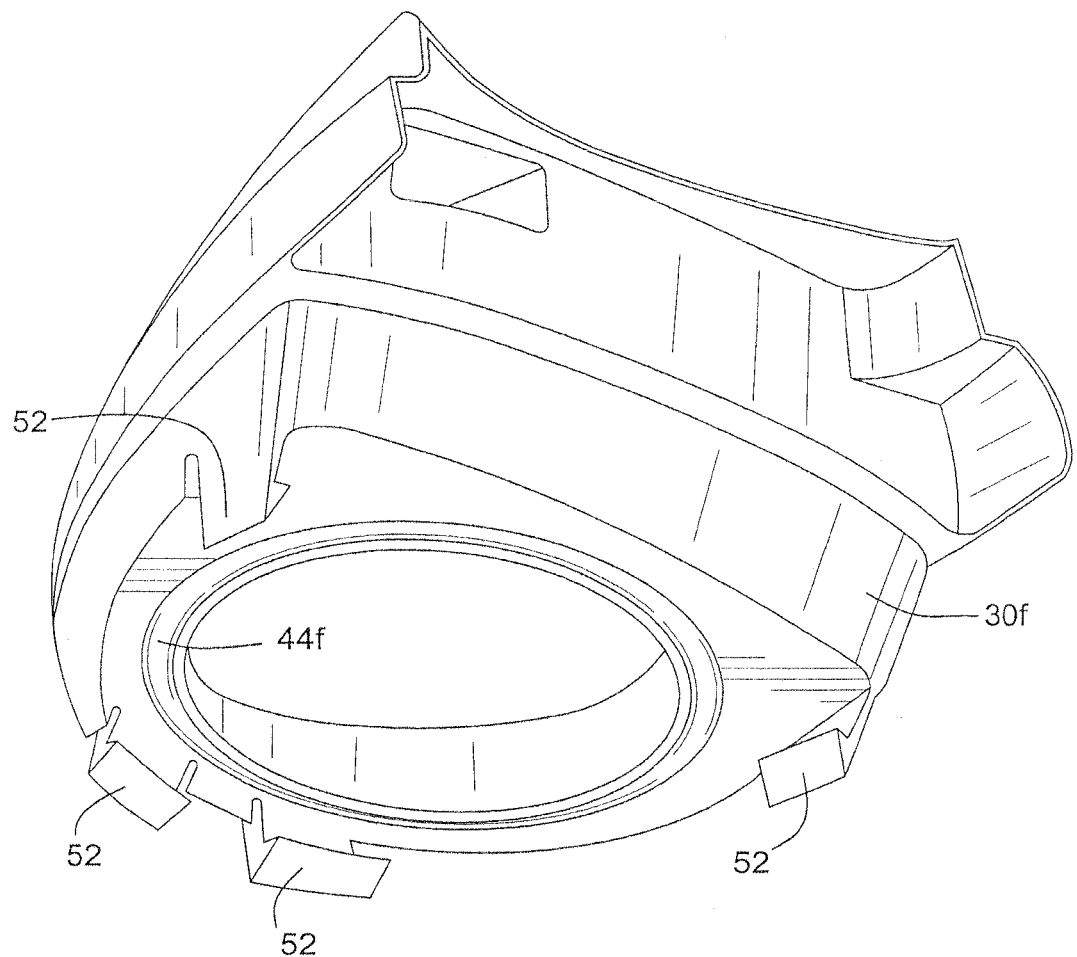
Figure 12A:
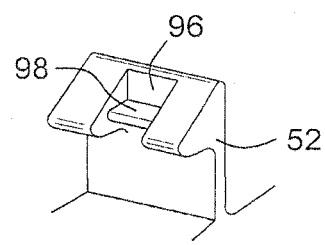

Referring to FIGS. 11 and 12, the tub base 30f includes a groove 44f for accommodating a seal 46f. Tabs 52 are provided on the tub base 30f and the base plate 26f is assembled to the tub base 30f by inserting the base plate 26f to the tube base 30f in the direction shown by the arrows in FIG. 11. The tabs 52 are resilient and the base plate 26f causes an elastic displacement of the tabs 52 upon insertion. The displaced tabs 52 remain somewhat displaced upon full insertion of the base plate 26f to bias the base plate 26f in contact with the seal 46f. Referring to FIG. 12a, the tabs 52 may include tamper evident projections. The tamper evident projections provide evidence of tampering with the base plate 26f in a situation in which the base plate 26f is designed to be removed only by technician. The tabs have a slot 96 with a fragile rib 98 which would crush if tampered with.

2.7 Tub Eighth Embodiment

Figure 13:
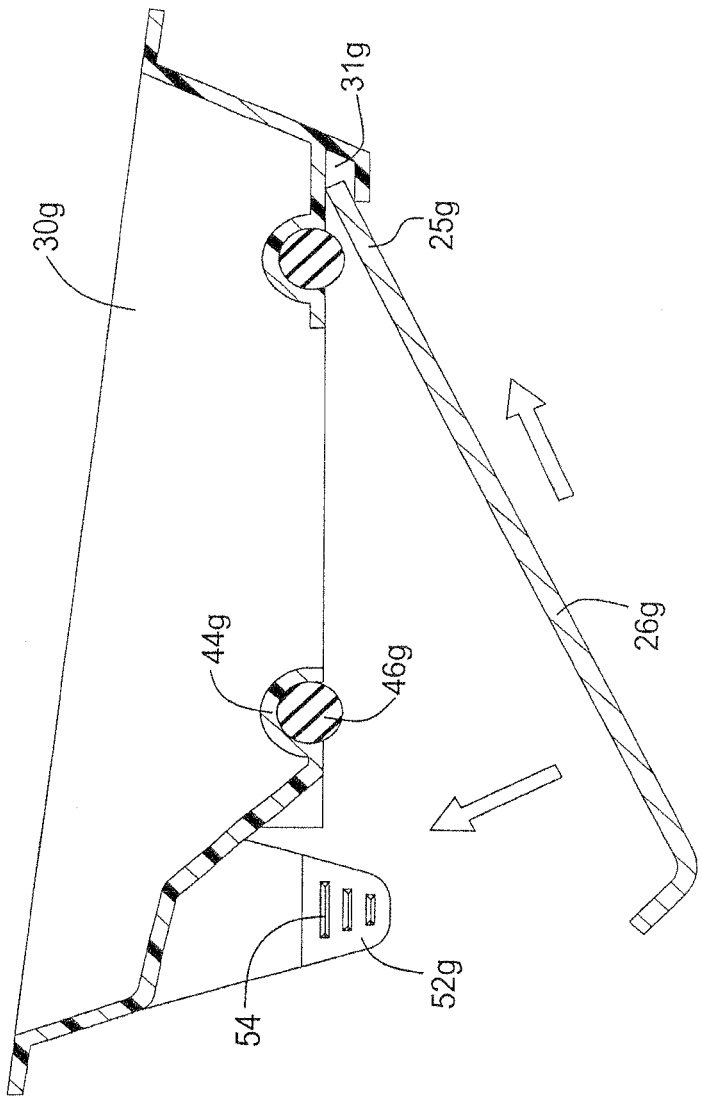
FIGS. 13 and 14 schematically illustrate a humidifier tub according to another sample embodiment of the present invention.
Figure 14:
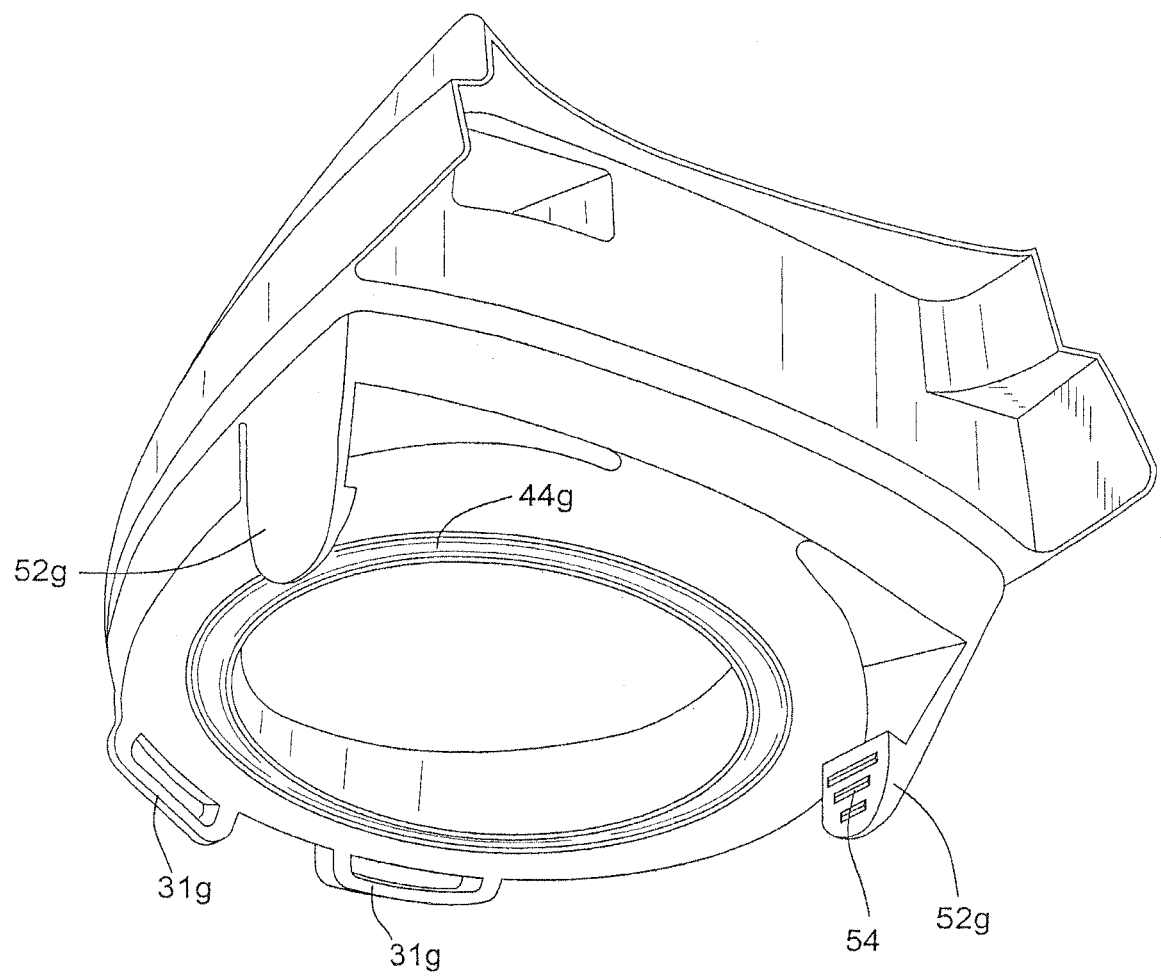

According to another embodiment of the present invention shown in FIGS. 13 and 14, alignment tabs 25g of the base plate 26g are inserted into alignment slots 31g in the tub base 30g. The opposite end of the base plate 26g is then pivoted toward the tub base 30g in the direction shown by the arrow in FIG. 13. The base plate 26g is pivoted into connection with a seal 46g which is accommodated in a recess 44g in the tub base 30g. Resilient tabs 52g are provided for securing the base plate 26g to the tub base 30g. The tabs 52g include textured finger grips 54.

2.8 Tub Ninth Embodiment

Figure 15:
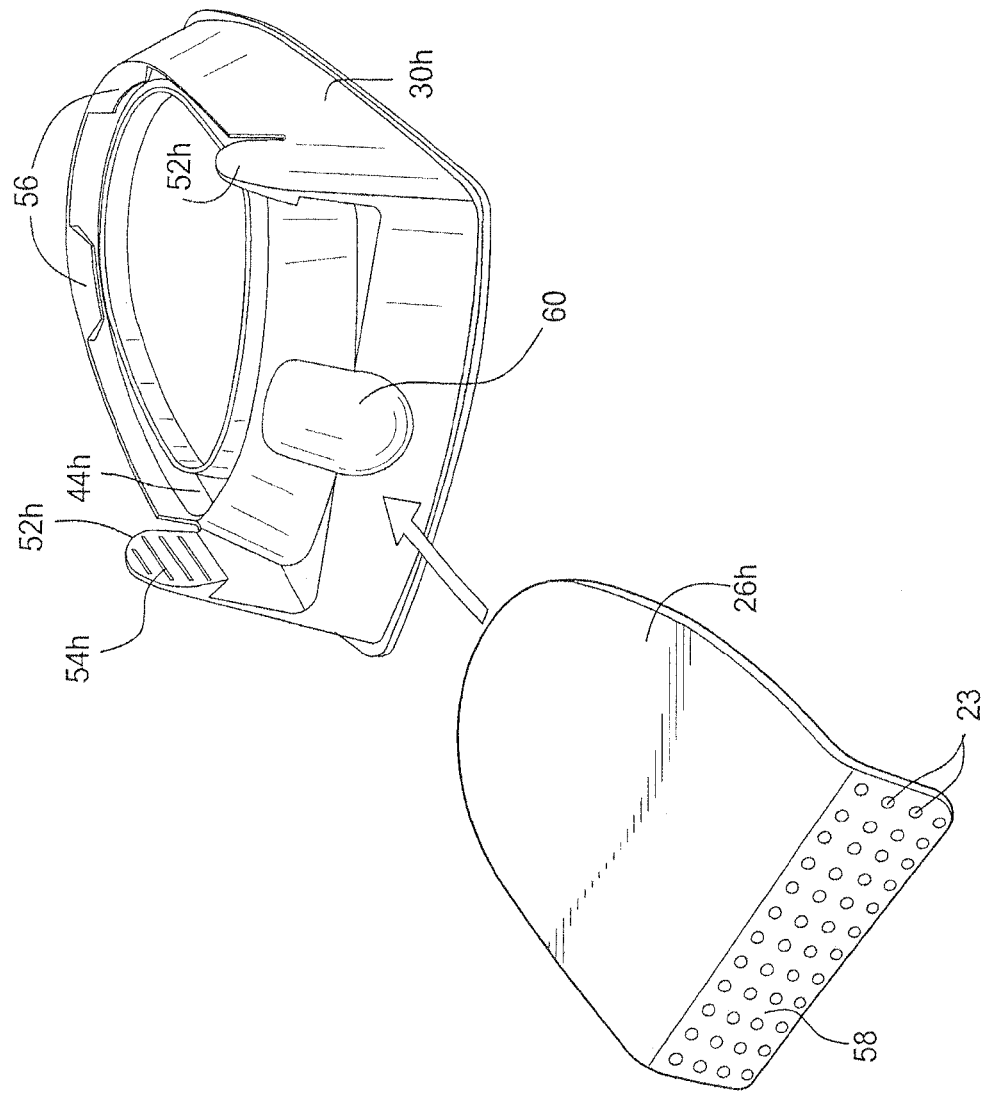
FIGS. 15 and 16 schematically illustrate a humidifier tub according to another sample embodiment of the present invention.
Figure 16:
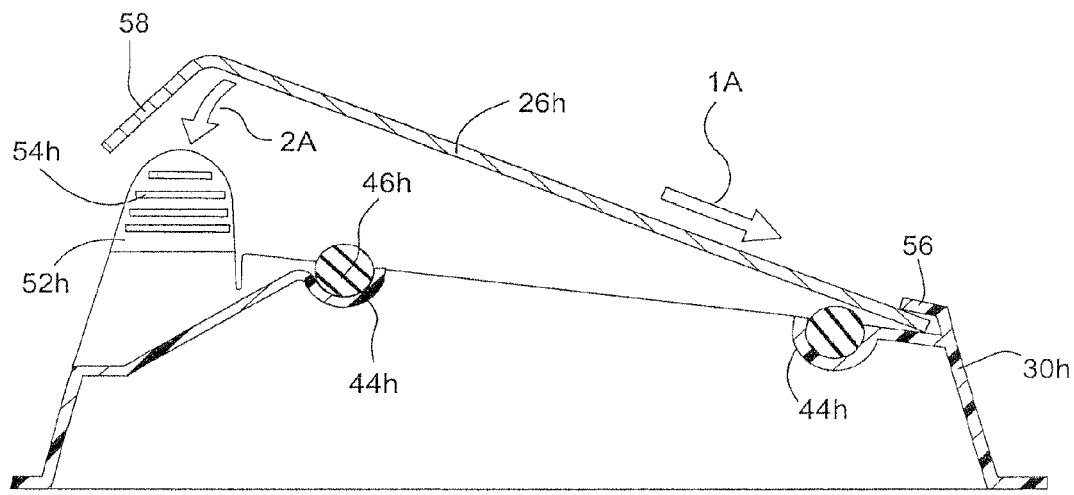

Referring to FIGS. 15 and 16, according to another embodiment of the present invention, the base plate 26h is attached to the tub base 30h in the direction shown by the arrow 1A then 2A in FIG. 16. Lips 56 on the tub base 30h receive the inserted end of the base plate 26h. As shown in FIG. 16, the base plate 26h is then pivoted into engagement with a seal 46h accommodated in groove 44h of the tub base 30h. The base plate 26h includes an inclined second end 58 which is pivoted past resilient tabs 52h which include finger grips 54h. The second end 58 of the base plate 26h may include a textured surface 23 to improve the user's grip on the base plate 26h. As shown in FIG. 15, a depression 60 is formed into the tub base 30h to facilitate insertion of a user's finger upon initial displacement of the base plate 26h to the disassembled position and to permit easier removal of the base plate 26h from the tub base 30h. The base plate 26h may be removed in the direction opposite to the arrow shown in FIG. 15.

2.9 Tub Tenth Embodiment

Figure 17:
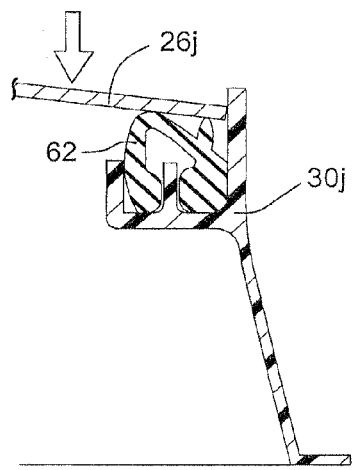
FIG. 17 schematically illustrates a humidifier tub according to another sample embodiment of the present invention.

Referring to FIG. 17, a seal 62 is provided between the base plate 26j and the tub base 30j. The seal 62 acts as a spring to bias the base plate 26j. The seal 62 may be used in any of the embodiments disclosed herein.

2.10 Tub Eleventh Embodiment

Figure 18:
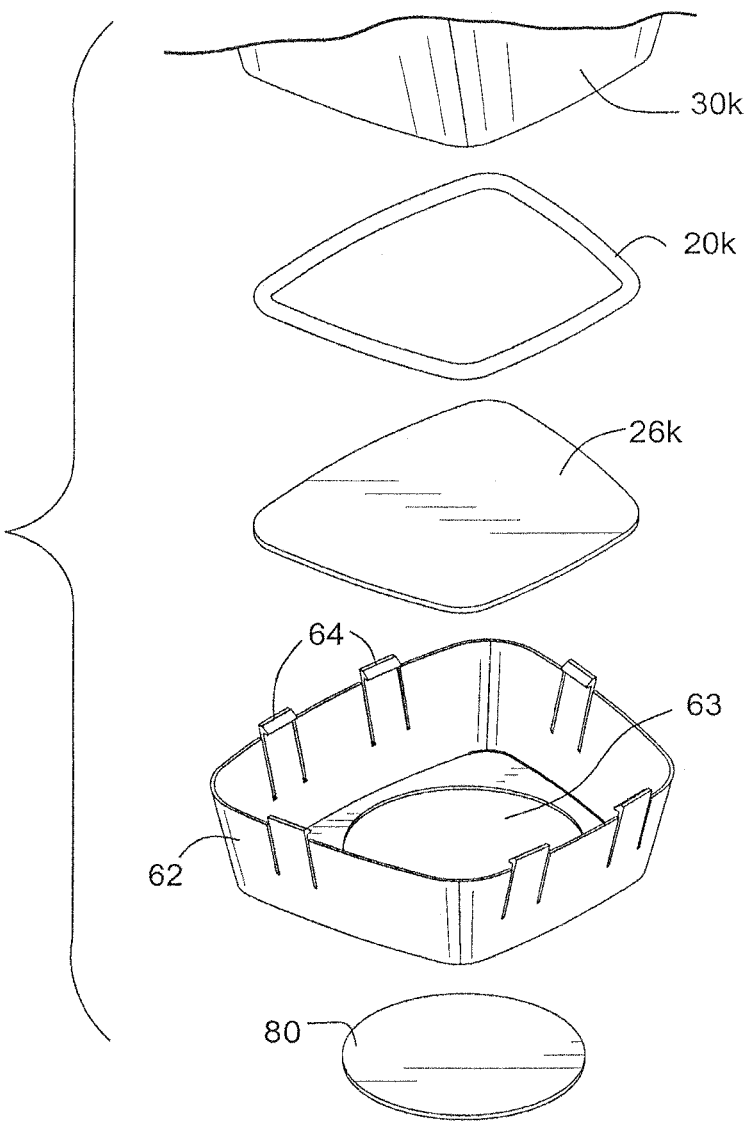
FIGS. 18 and 19 schematically illustrate a humidifier tub according to another sample embodiment of the present invention.
Figure 19:
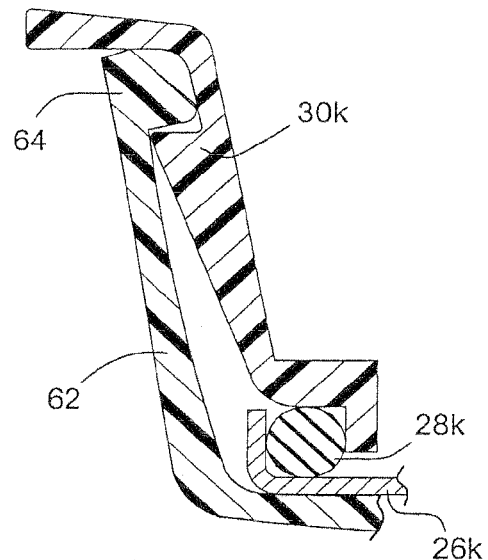
Figure 20:
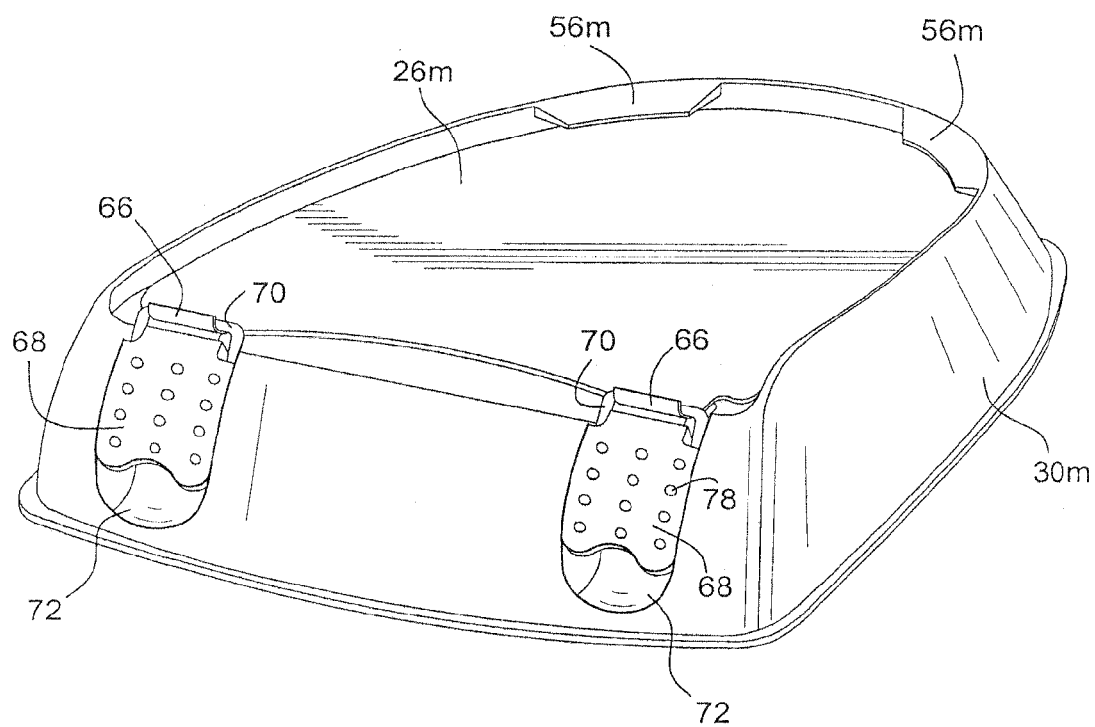
FIGS. 20-23 schematically illustrate a humidifier tub according to another sample embodiment of the present invention.
Figure 21:
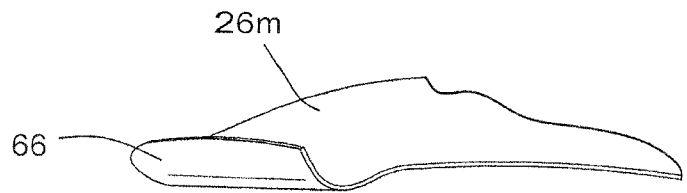
Figure 22:
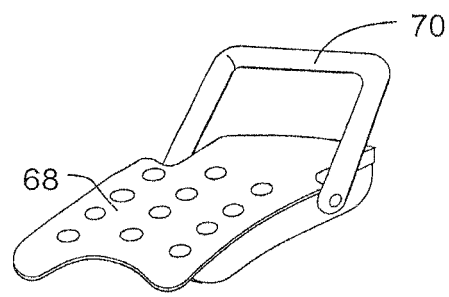
Figure 23:
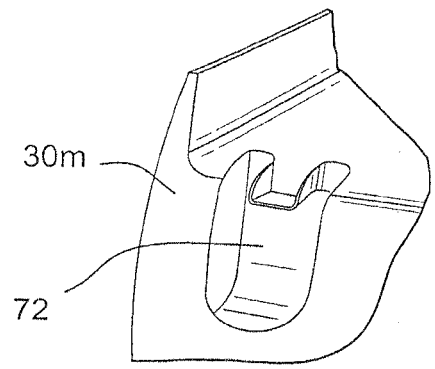

Referring to FIGS. 18 and 19, a base unit 62 includes latches 64 around a top perimeter to lock the tub base 30k into engagement with the seal 28k. The base plate 26k is provided between the base unit 62 and the tub base 30k and the seal 28k is sandwiched between the base plate 26k and the tub base 30k. As shown in FIG. 19, the latches 64 secure the contact between the tub base 30k and the seal 28k and the contact between the seal 28k and the base plate 26k to form a substantially waterproof seal. The base unit 62 includes an opening 63. A heating element or unit 80, such as a ceramic plate, is received in the opening 63 so as to be in contact with the base plate 26k when the tub is assembled in the base unit 62. Contact between the base plate 26k and the heating element 80 is maintained by the engagement of the latches 64 with the tub base 30k. The latches 64 bias the tub base 30k toward the base plate 26k thus biasing the base plate 26k into contact with the heating element 80. The base unit 62 may be provided as an integral part of the casing 12, or separate from the casing.

2.11 Tub Twelfth Embodiment

According to another embodiment of the present invention shown in FIGS. 20-23, a first end of the base plate 26m is inserted into the tub base 30m and held in place by lips 56m. The second, opposite end of the base plate 26m is secured by overcenter cams 68 that engage cam levers 66 provided on the base plate 26m. Each overcenter cam 68 is pivotably attached to the tub base 30m so as to be received in a recess 72 into the tub base 30m. Each overcenter cam 68 includes a linkage 70 which engages the cam lever 66 of the base plate 26m to secure the attachment of the base plate 26m to the tub base 30m. A surface texture 78, such as depressions or projections, may be provided to the overcenter cams 68 that improve a user's grip on the overcenter cams 68.

2.12 Tub Thirteenth Embodiment

Figure 24:
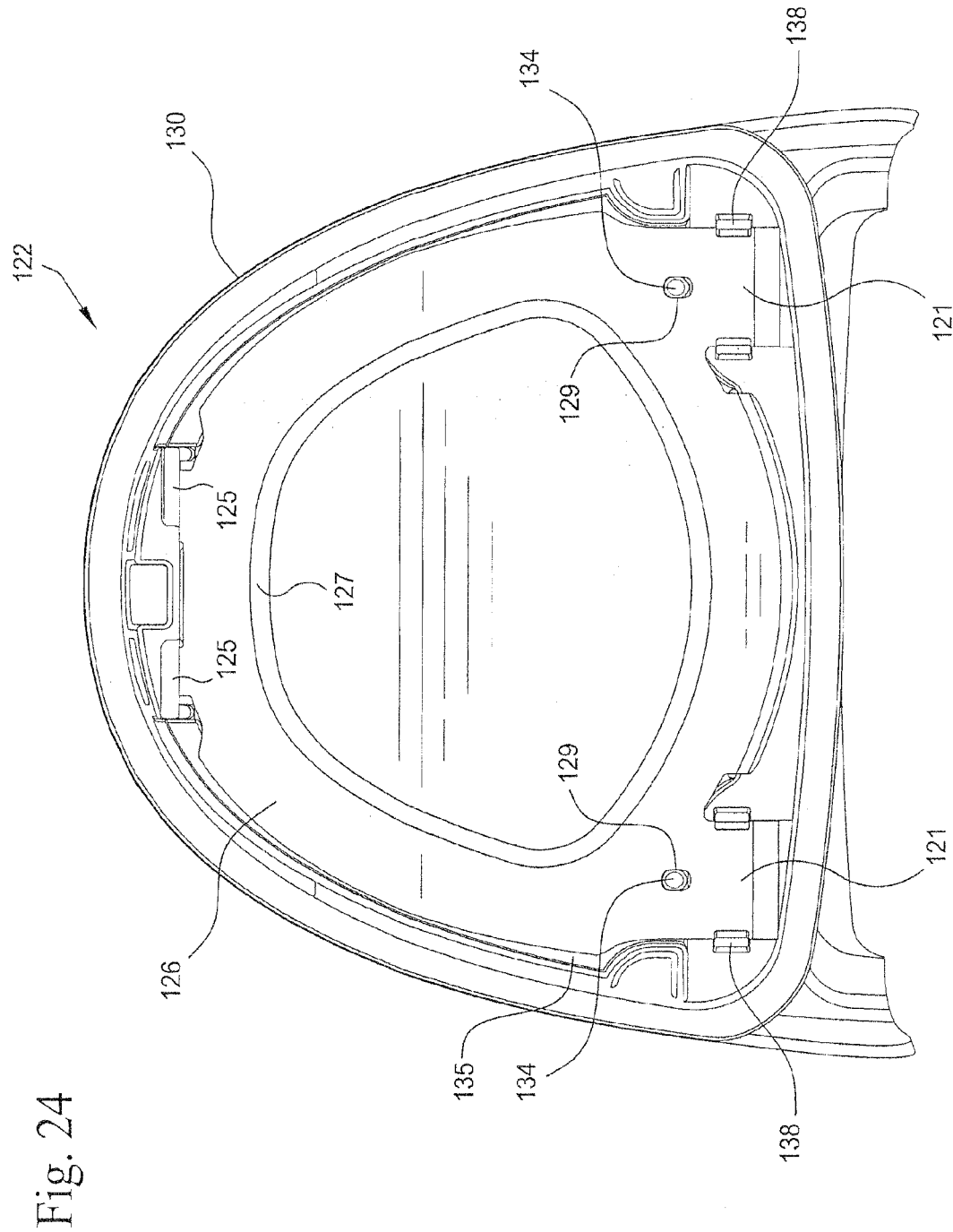
FIGS. 24-26 schematically illustrate a humidifier tub according to another sample embodiment of the present invention.
Figure 25:
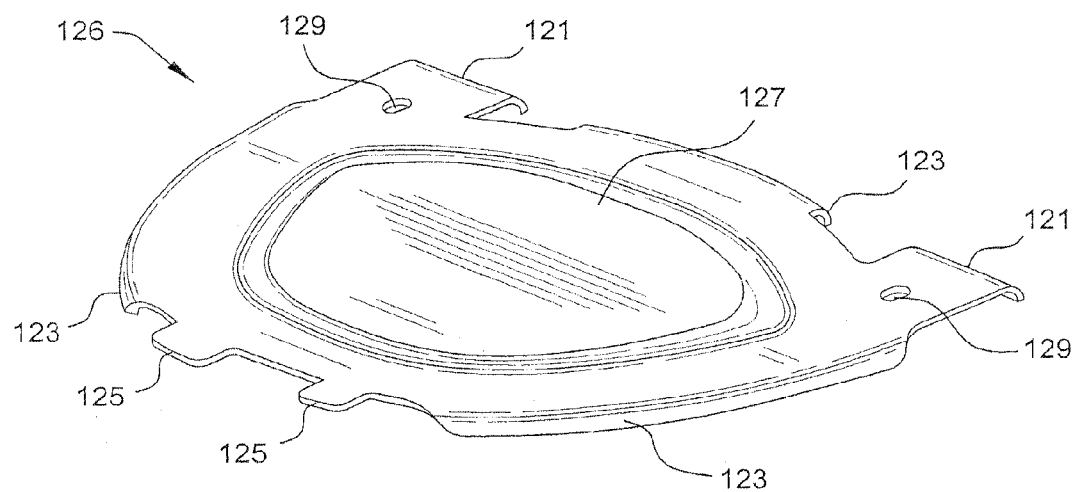
Figure 26:
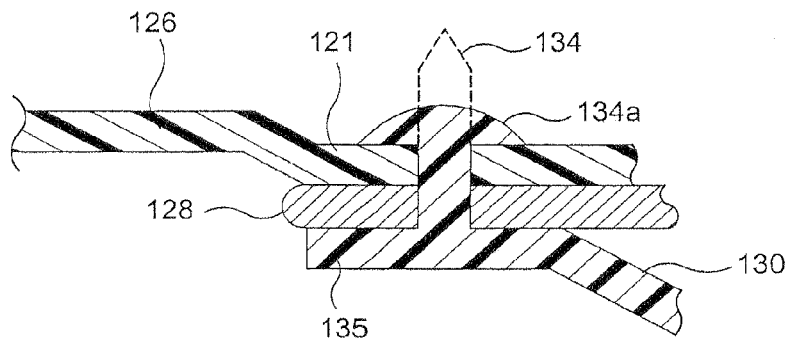
Figure 27:
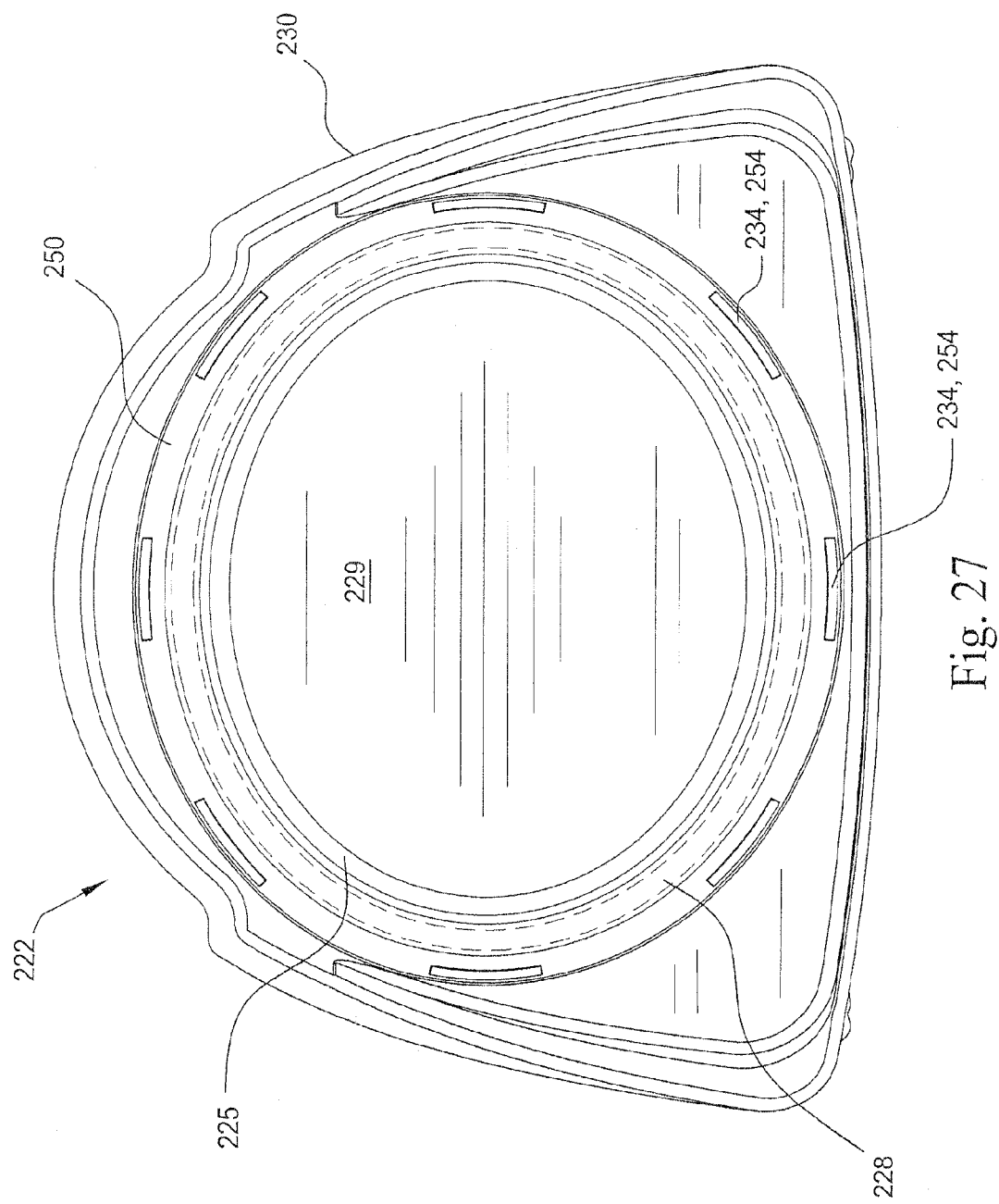
FIGS. 27-32 schematically illustrate a humidifier tub according to another sample embodiment of the invention.

Referring to FIGS. 24-26, another sample embodiment of the humidifier tub 122 may comprise a tub base 130 and a base plate 126. A seal 128 (FIG. 26) is compressed between a bottom peripheral edge 135 of the tub base 130 and the base plate 126 to form a water tight tub 122. The base plate 126 may comprise a stamped ring 127, which may have a shape corresponding to the seal 128.

The base plate 126 may be permanently attached to the tub base 130 by tabs, or snaps, 138 formed in the tub base 130 that engage latch tabs 121 on the base plate 126. The tabs, or snaps, 138 may be similar to the tabs shown, for example, in FIGS. 11-16. The snaps 138 are arranged in sets of two, symmetrical around the center of the tub base 130, and together with alignment tabs 125 of the base plate 126 that are inserted into alignment slots (not shown) of the tub base 130, form a generally triangular compression region for the seal 128.

The snaps 138 grip opposite sides of the latch tabs 121 on the base plate 126 and provide the force for compressing the seal 128 and hold the base plate 126 in position for heat staking. As shown in FIGS. 24-26, the base plate 126 comprises apertures 129 in the latch tabs 121. The tub base 130 further includes heat stakes 134 that extend through the apertures 129 in the latch tabs 121, as shown in FIG. 26. The heat stakes 134 are passed through apertures in the seal 128 and through the apertures 129 in the base plate 126. The top of the heat stake is then melted, for example using a heated probe or an ultrasonic horn, to create a blob of plastic. The dome 134a of the heat stake 134 assists in holding the base plate 126 in position in a permanent manner that is clearly visible.

2.13 Tub Fourteenth Embodiment

Referring to FIGS. 27-32, a humidifier tub 222 according to another sample embodiment comprises a tub base 230 and a base plate 226. The base plate 226 may be formed, for example, as a generally oval stainless steel plate pressed from coil. The base plate 226 comprises a rib 225 that isolates a contact surface 227 from forces that connect the base plate 226 and the tub base 230 and maintain a flat surface 229 of the base plate. A seal 228 is provided on the contact surface 227.

The base plate 226 is connected to the tub base 230 by a snap ring 250. The snap ring 250 includes a contact surface 252. When the tub is assembled, the contact surface 252 engages the bottom of the seal 228 and the top of the seal 228 is engaged by the contact surface 227 of the base plate 226. The seal 228 is compressed between the contact surface 252 of the snap ring 250 and the contact surface 227 of the base plate 226.

Figure 28:
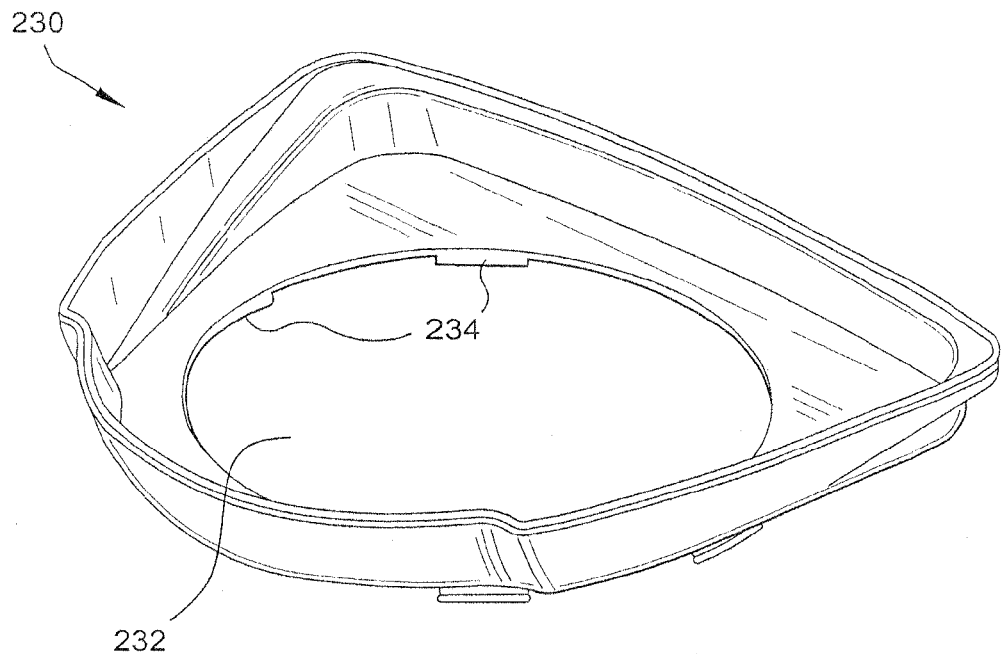
Figure 29:
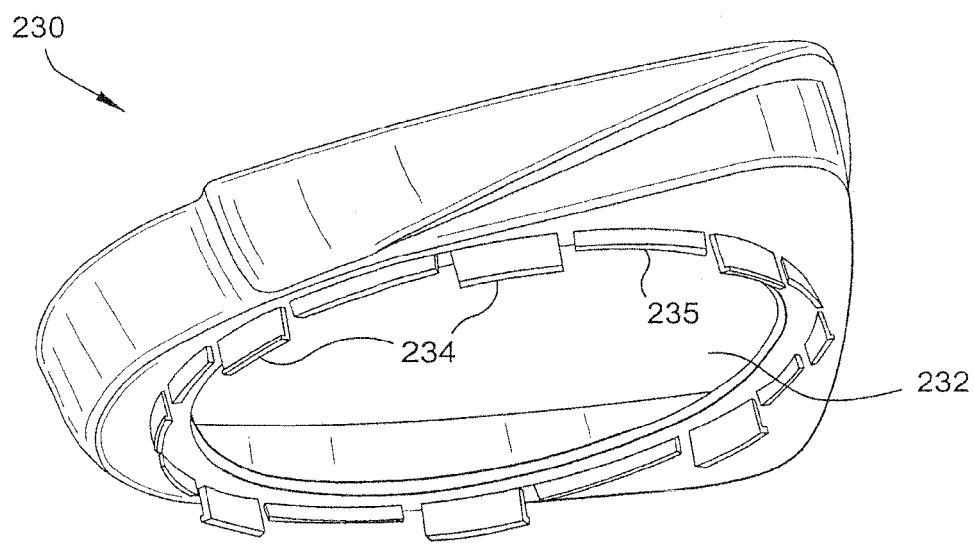
Figure 30:
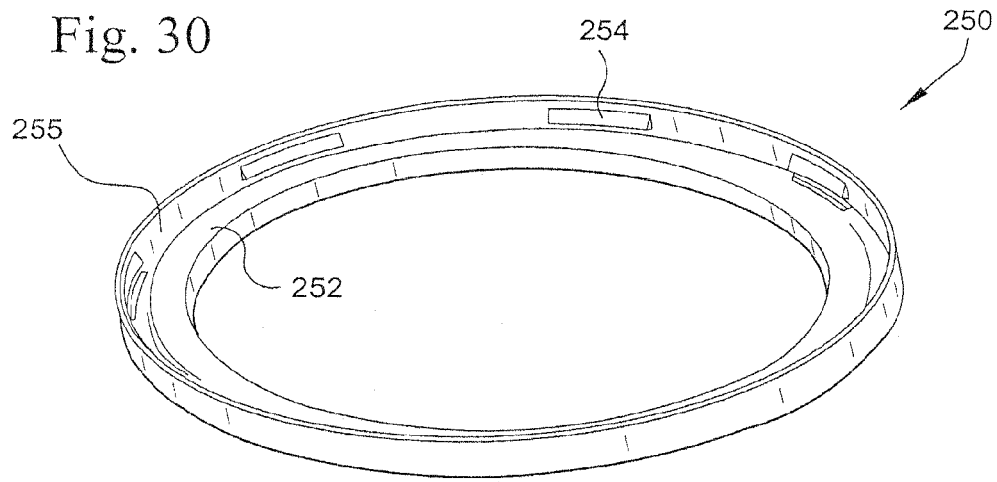
Figure 31:
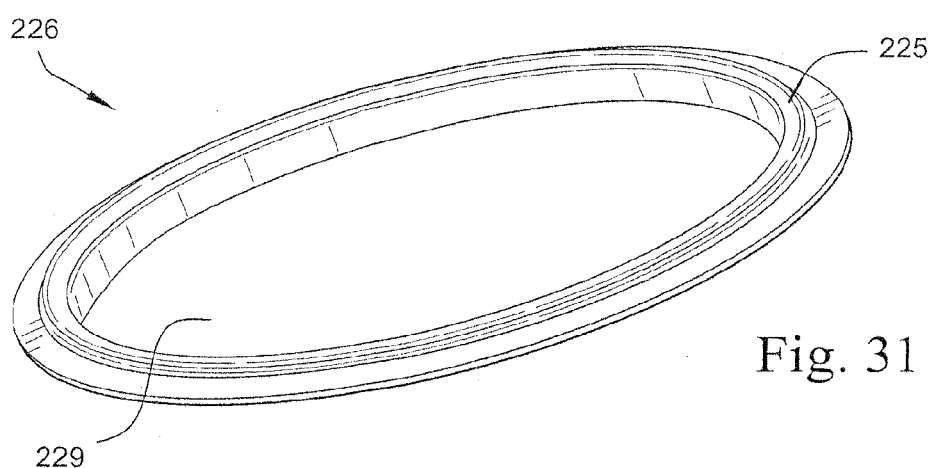
Figure 32:
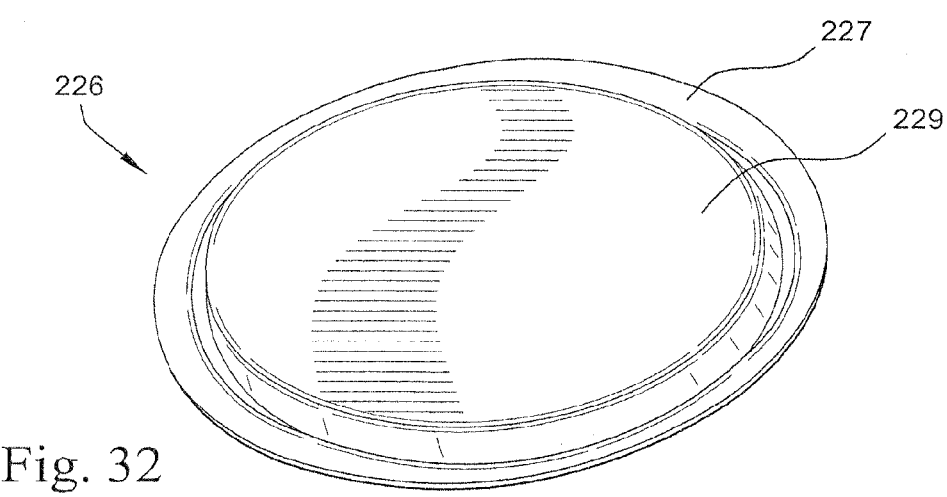

As shown in FIGS. 28-30, the snap ring 250 is connected to the tub base 230, with the base plate 226 in between, by the engagement of snaps 254 formed on the inner periphery of the snap ring 250 that engage snaps 234 formed around the periphery of an opening 232 in the tub base 230. The periphery of the opening 232 of the tub base 230 also includes a plurality of alignment or guide tabs 235 that are received in a channel 255 in the periphery of the snap ring 250. The alignment or guide tabs 235 are received between the snaps 254 of the snap ring 250 when the snap ring 250 is connected to the tub base 230. The alignment or guide tabs 235 thus prevent the snap rings 250 from rotating relative to the tub base 230 and disengagement of the snaps 234, 254.

As shown in FIG. 29, the alignment or guide tabs 235 are provided between the snaps 234 around the periphery of the opening 232. Although eight snaps 234, 254 are shown on the tub base 230 and snap ring 250, respectively, it should be appreciated that any number of snaps may be provided. It should also be appreciated that the opening 232, the snap ring 250 and the base plate 226 may have a shape other than oval, for example circular.

The snap ring 250 retains the base plate 226 to the tub base 230 and prevents the removal of the base plate 226 from the tub base 230. The contact surfaces 252, 227 put pressure on the seal 228 and compress the seal 228 between the snap ring 250 and the base plate 226.

The seal 228 may be a face oriented O-ring. A face oriented O-ring may be used, as the seal is not relied on to retain the base plate 226, which eliminates the effect of friction on the installation of the base plate 226 and retention of the base plate 226. The face oriented O-ring 228 has a shape generally corresponding to the contact surfaces 227, 252 and has a width that is sufficient to permit some misalignment between the tub base 230 and the base plate 226 while still maintaining the substantially waterproof seal. This provides a more reliable and robust seal.

The tub base 230, the base plate 226 and the snap ring 250 are designed to be assembled along a single axis and in one plane. This enables the tub 222 assembly process to be automated, which reduces the cost of manufacture and part-to-part variation.

2.14 Tub Fifteenth Embodiment

Figures 33, 34:
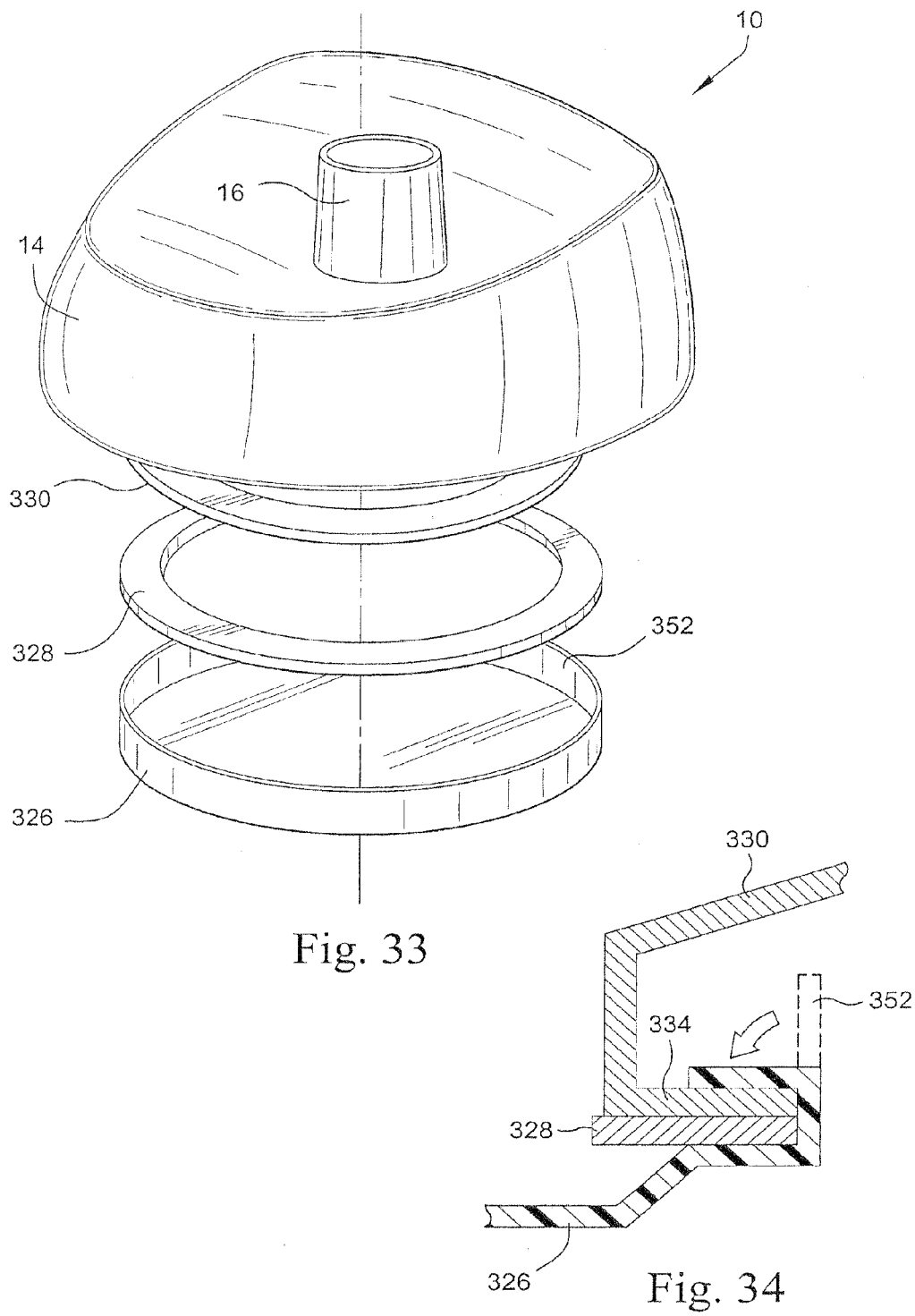
FIGS. 33 and 34 schematically illustrate a humidifier and humidifier tub according to another sample embodiment of the invention.

Referring to FIGS. 33 and 34, a humidifier 10 according to another sample embodiment comprises a lid 14 having an outlet 16 configured for connection to a hose or conduit. A tub of the humidifier comprises a tube base 330, a base plate 326 and a seal 328 provided between the tub base 330 and the base plate 326. The base plate 326 comprises a peripheral, e.g. annular, wall 352 that may be folded as shown in FIG. 34 to compress the seal 328 between the base plate 326 and a bottom edge 334 of the tub base 330. The peripheral wall 352 may be folded, for example, by bending the peripheral wall 352, to compress the seal 328 between the bottom edge 334 and the base plate 326. The base plate 326 may be made, for example, for metal, such as stainless steel.

2.15 Tub Sixteenth Embodiment

Figure 35:
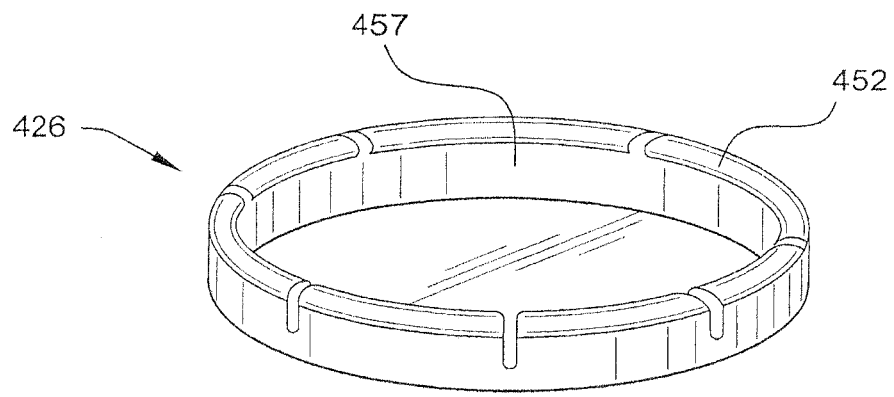
FIGS. 35 and 36 schematically illustrate a humidifier tub according to another sample embodiment of the invention.
Figure 36:
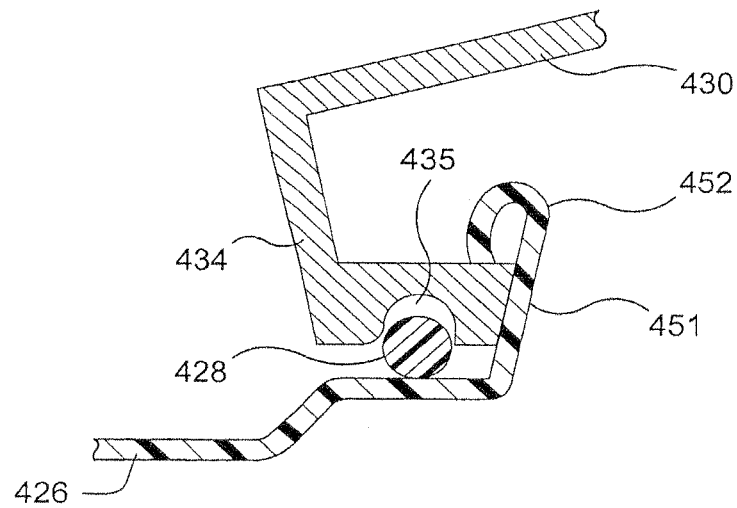

Referring to FIGS. 35 and 36, the base plate 426 of the humidifier tub may comprise an annular wall 451 that includes a curved, or hooked, end 452 that is configured to engage the bottom peripheral edge 434 of the tub base 430. The bottom peripheral edge 434 may include a groove, or channel, 435 configured to accommodate a seal 428, e.g. an O-ring, that is compressed between the base plate 426 and the tub base 430 when the curved end 452 of the base plate 426 engages the bottom peripheral edge 434 of the tub base 430.

2.16 Tub Seventeenth Embodiment

Figure 37:
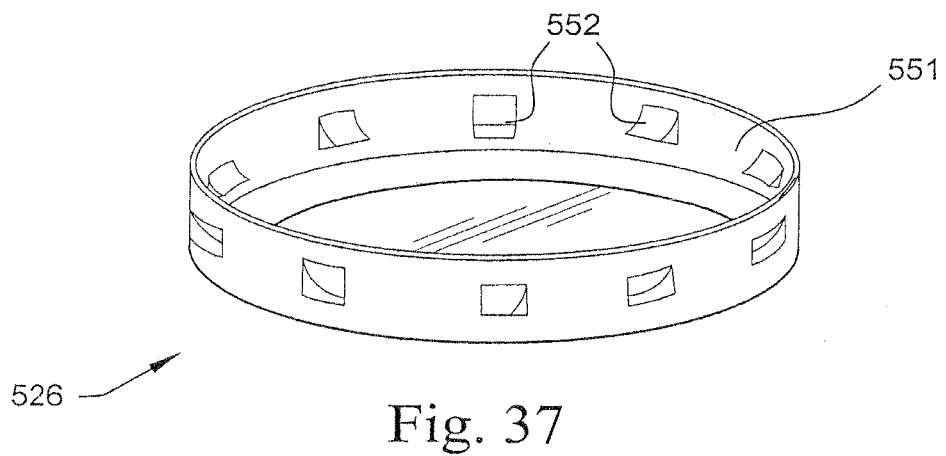
FIGS. 37 and 38 schematically illustrate a humidifier tub according to another sample embodiment of the invention.
Figure 38:
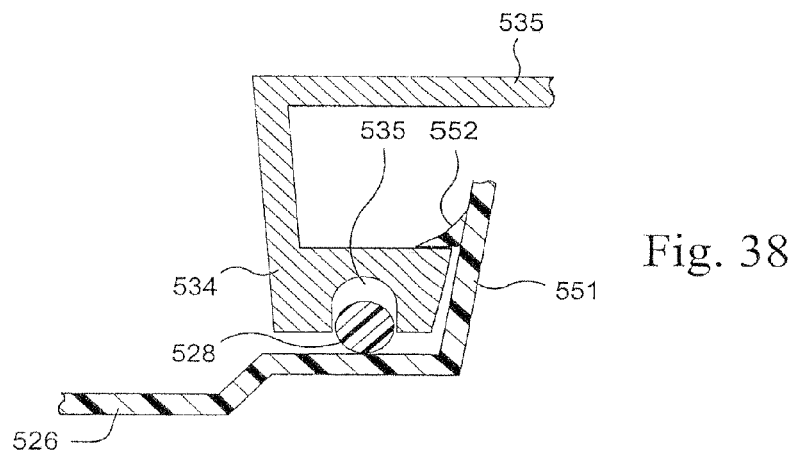

Referring to FIGS. 37 and 38, the base plate 526 of the humidifier tub may comprise an annular wall 551 having a plurality of resilient tabs 552 formed therein. The resilient tabs 552 are configured to engage the bottom peripheral edge 534 of the tub base 530 to compress a seal 528, e.g. an O-ring, between the base plate 526 and the tub base 530. The bottom peripheral edge 534 of the tub base 530 may comprise a groove, or channel, 535 to accommodate the seal 528.

2.17 Tub Eighteenth Embodiment

Figure 39:
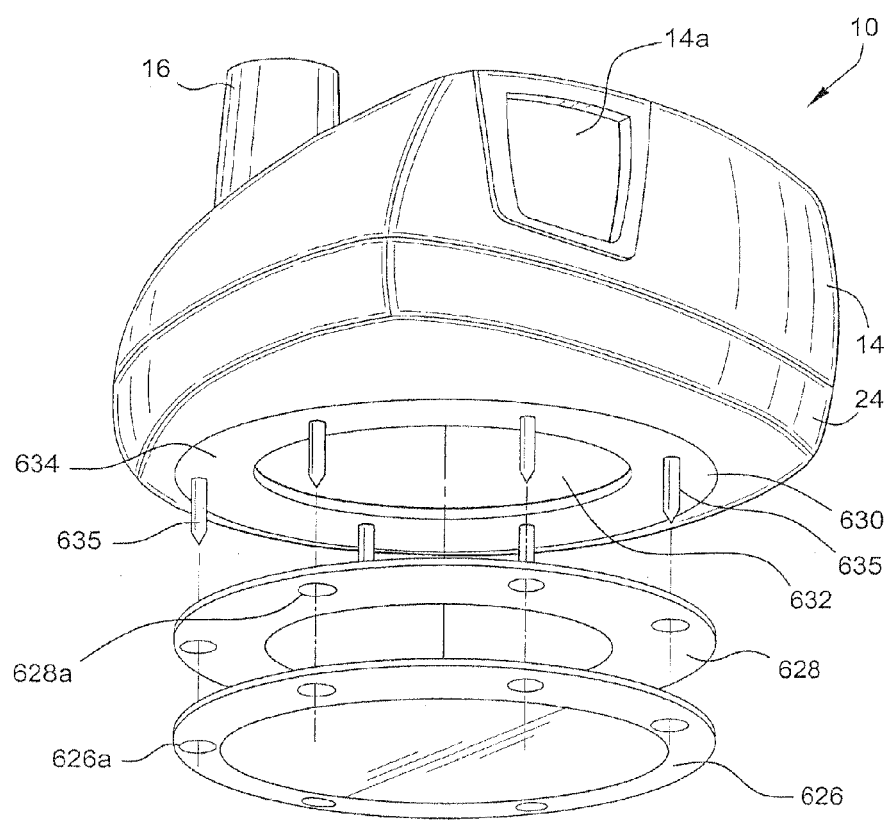
FIG. 39 schematically illustrates a humidifier and humidifier tub according to another sample embodiment of the invention.
Figure 40:
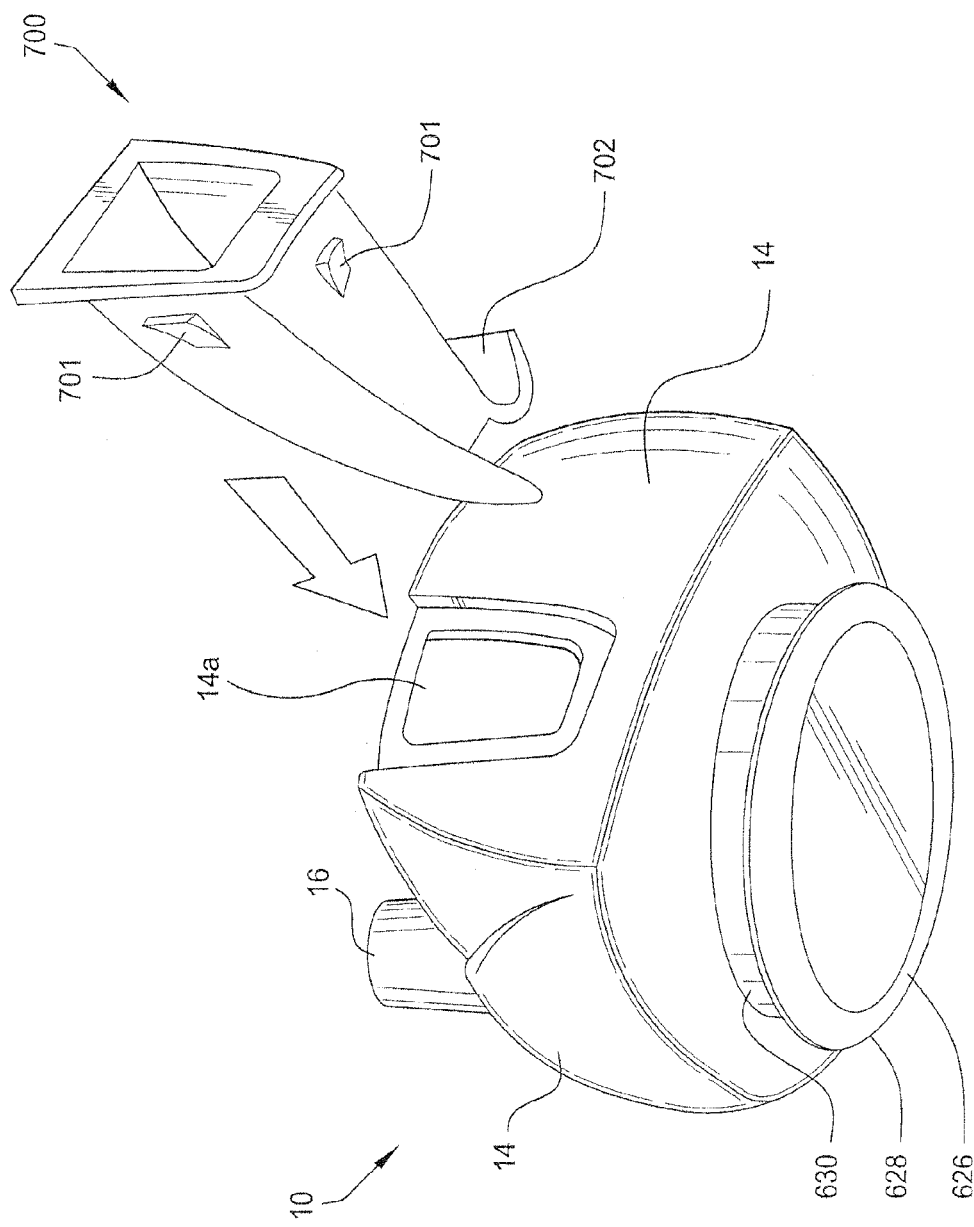
FIG. 40 schematically illustrates a humidifier according to another sample embodiment of the invention.

Referring to FIGS. 39 and 40, a humidifier 10 may comprise a lid 14 having an outlet 16 configured for connection to a hose or conduit. The humidifier may also comprise a water container comprising a tub including a tub lid 24 and a tub. The tub comprises a tube base 630 and a base plate 626. The tub base 630 may comprise an opening 632 surrounded by a bottom peripheral edge 634. The base plate 626 is configured to cover the opening 632 and a seal 628 is provided to seal the connection of the base plate 626 to the tub base 630. The tub base comprises heat stakes 635 that are received in apertures 626a, 628a in the base plate 626 and seal 628, respectively. The ends of the heat stakes 635 are melted, for example by a heated probe or ultrasonically, to form a dome portion similar to the manner described above to permanently connect the base plate 626 to the tube base 630.

As shown in FIG. 40, a cross beam channel 700 is configured for insertion into an inlet 24a of the tub lid 24. The cross beam channel includes flexible tabs that permit insertion of the cross beam channel 700 into the inlet 24a, but prevent removal of the cross beam channel 700 after insertion. The cross beam channel also comprises a curved end 702. The curved end 702 has the dual function of guiding the inlet air over the surface of the water, and to provide spill back protection.

The base plate of the embodiments of the present invention may be formed of a material that provides good heat conduction, for example metal. The base plate may be formed, for example, of stainless steel. As discussed above, the base plate is configured to be in contact with a heating device, such as a ceramic heating pad or plate, to increase the amount of water vapor in the supplied air. A stainless steel base plate transfers more heat to the water in the tub. Increasing the heat transfer from the base plate to the water in the container by using a stainless steel plate also reduces the energy consumption of the humidifier. Transferring more heat to the water in the tub also allows for an increase in the capacity of the tub while maintaining the required level of humidification.

The use of a stamped stainless plate for the base plate also reduces the cost of the humidifier as it is less expensive to provide a stamped plate than a machined plate. To further reduce costs, the tub base may be formed of a plastic material. The tub according to the present invention may also be removed from the humidifier and easily cleaned, for example by placing the tub in a dishwasher.

Although the embodiments described above include seals that are separate from the tub base and the base plate, it should be appreciated that the seal may be formed so as to be integral with the tub base or the base plate, for example by overmolding the seal with the tub base.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. Furthermore, each individual component of any given assembly, one or more portions of an individual component of any given assembly, and various combinations of components from one or more embodiments may include one or more ornamental design features. In addition, while the invention has particular application to patients who suffer from OSA, it is to be appreciated that patients who suffer from other illnesses (e.g., congestive heart failure, diabetes, morbid obesity, stroke, barriatric surgery, etc.) can derive benefit from the above teachings. Moreover, the above teachings have applicability with patients and non-patients alike in non-medical applications.

What is claimed is:

1. A humidifier adapted to be connected to a flow generator, the humidifier comprising:
   a humidifier cradle having a bottom surface with a heating element and a side face configured to engage the flow generator and facilitate attachment of the humidifier to the flow generator;
   a humidifier lid hinged to the humidifier cradle, the humidifier lid including a seal and an air outlet pipe configured to be connected to a hose to deliver a supply of pressurized, breathable gas to a patient via a patient interface; and
   a water container configured to store a supply of water used to humidify the supply of breathable gas and configured to be received by the humidifier cradle, the water container comprising:
      a tub lid; and
      a tub adapted to be coupled to the lid, the tub comprising:
         a base plate with a perimeter including a plurality of tabs with apertures;
         a tub base with a bottom peripheral edge that includes a rim defining an opening, the tub base including a plurality of tab receiving portions configured to receive the plurality of base plate tabs and a plurality of heat stakes that extend through the apertures in the base plate tabs, each heat stake having a melted head portion that is larger than a corresponding aperture; and
         a tub seal positioned between the base plate and the tub base,
   wherein the humidifier lid is pivotable to an open position that accommodates insertion of the water container into the humidifier cradle, and pivotable to a closed position that secures the water container in an operable position in the humidifier cradle,
   wherein the heating element is configured to contact the base plate of the tub when the water container is inserted into the humidifier cradle,
   wherein the humidifier lid is configured to be raised with the hose still attached,
   wherein the humidifier lid seal is configured to engage the tub lid when the humidifier lid is in the closed position, and
   wherein the tub lid is configured to communicate with the air outlet pipe when the humidifier lid is in the closed position.

2. A humidifier according to claim 1, wherein the melted head portions of the heat stakes assist in holding the base plate against the tub base.

3. A humidifier according to claim 2, wherein the melted head portions are in the shape of a dome.

4. A humidifier according to claim 3, wherein the heat stakes comprise plastic.

5. A humidifier according to claim 4, wherein the tub seal is an O-ring.

6. A humidifier according to claim 5, wherein the tub seal is compressed between the base plate and the bottom peripheral edge of the tub base.

7. A humidifier according to claim 5, wherein the bottom peripheral edge of the tub base includes a channel configured to accommodate the tub seal.

8. A CPAP machine comprising:
   a flow generator; and
   the humidifier of claim 1.

9. A humidifier according to claim 1, wherein the tub base comprises an alignment structure configured to align the base plate with the opening in the tub base.

10. A humidifier according to claim 9, wherein the base plate comprises a stamped ring having a shape corresponding to the seal.

11. A humidifier according to claim 10, wherein a central portion of the base plate is recessed with respect to the perimeter of the base plate.

12. A humidifier according to claim 10, wherein a central portion of the base plate is recessed with respect to the tabs with apertures.

13. A humidifier according to claim 1, wherein the base plate has raised edges.

14. A humidifier according to claim 1, wherein the tub seal has a shape that generally corresponds to the bottom peripheral edge of the tub base.

15. A tub for a humidifier configured to hold a supply of water, the tub comprising:
   a tub lid;
   a tub base adapted to be coupled to the tub lid;
   a base plate formed of a heat conducting material and adapted to be coupled to the tub base;
   a seal positioned between the base plate and the tub base; and
   a retaining mechanism with at least one projection that projects from the tub base through the heat conducting material and is configured to force the base plate against the seal so that the seal is secured against the tub base,
   wherein the base plate comprises a plurality of tabs configured to be received by a plurality of tab receiving portions in the tub base, and
   wherein the plurality of tabs share a common plane parallel to the base plate.

16. A tub according to claim 15, wherein the at least one projection comprises a stake extending from the tub base through an aperture in the base plate, the stake being configured to be melted to maintain the seal between the tub base and the base plate.

17. A tub according to claim 16, wherein the at least one projection comprises a plurality of projections, each projection comprising a stake and the aperture in the base plate is among a plurality of apertures in the base plate adapted to receive the plurality of stakes.

18. A tub according to claim 17, wherein the apertures are provided in the tabs of the base plate.

19. A tub according to claim 18, wherein the stakes include melted head portions that are larger than the apertures and are configured to assist in holding the base plate against the tub base.

20. A tub according to claim 19, wherein the melted head portions are in the shape of a dome.

21. A tub according to claim 20, wherein the stakes comprise plastic.

22. A tub according to claim 21, wherein the stakes are configured to be heated ultrasonically or by a heated probe.

23. A humidifier comprising:
   the tub of claim 15;
   a humidifier cradle configured to receive the tub; and
   a humidifier lid hinged to the humidifier cradle.

24. A tub according to claim 15, wherein the seal is sandwiched between the base plate and the tub base.

25. A tub for a humidifier configured to hold a supply of water, the tub comprising:
   a base plate with raised edges, a perimeter of the base plate including a plurality of tabs with apertures;
   a tub base with a bottom peripheral edge that includes a rim defining an opening, the tub base including a plurality of tab receiving portions configured to receive the plurality of base plate tabs and a plurality of stakes that extend through the apertures in the base plate tabs, each stake having a melted head portion that is larger than a corresponding aperture;

a seal positioned between the base plate and the tub base; and a tub lid adapted to be coupled to the tub base, wherein the plurality of tabs of the base plate are comprised of heat conducting material, and wherein the plurality of tabs share a common plane parallel to the base plate.

26. A tub according to claim 25, wherein the melted head portions of the stakes assist in holding the base plate against the tub base.

27. A tub according to claim 26, wherein the melted head portions are in the shape of a dome.

28. A tub according to claim 27, wherein the stakes comprise plastic.

29. A tub according to claim 28, wherein the seal is an O-ring.

30. A tub according to claim 25, wherein tub seal is compressed between the base plate and the bottom peripheral edge of the tub base.

31. A tub according to claim 25, wherein the bottom peripheral edge of the tub base includes a channel configured to accommodate the tub seal.

32. A humidifier comprising:
the tub of claim 25;
a humidifier cradle configured to receive the tub; and
a humidifier lid hinged to the humidifier cradle.

33. A tub according to claim 25, wherein the entire base plate is formed of a heat conducting material.

34. A humidifier adapted to be connected to a flow generator, the humidifier comprising:
a humidifier cradle having a bottom surface with a heating element and a side face configured to engage the flow generator and facilitate attachment of the humidifier to the flow generator;
a humidifier lid hinged to the humidifier cradle, the humidifier lid including a seal and an air outlet pipe configured to be connected to a hose to deliver a supply of pressurized, breathable gas to a patient via a patient interface; and
a water container configured to store a supply of water used to humidify the supply of breathable gas and configured to be received by the humidifier cradle, the water container comprising:
a tub lid; and
a tub adapted to be coupled to the lid, the tub comprising:
a base plate with a plurality of apertures surrounding a central portion of the base plate, the apertures being located at a periphery of the base plate;
a tub base with a bottom peripheral edge that includes a rim defining a substantially circular opening, the tub base including a plurality of heat stakes that project from the tub base and extend through the apertures in the base plate, each heat stake having a melted head portion that is larger than a corresponding aperture; and
wherein the humidifier lid is pivotable to an open position that accommodates insertion of the water container into the humidifier cradle, and pivotable to a closed position that secures the water container in an operable position in the humidifier cradle,
wherein the central portion of the base plate is substantially circular and covers the substantially circular opening of the tub base,
wherein the plurality of heat stakes and the plurality of apertures are equidistant from the center of the central portion of the base plate,
wherein the heating element is configured to contact the base plate of the tub when the water container is inserted into the humidifier cradle,
wherein the humidifier lid is configured to be raised with the hose still attached,
wherein the humidifier lid seal is configured to engage the tub lid when the humidifier lid is in the closed position, and
wherein the tub lid is configured to communicate with the air outlet pipe when the humidifier lid is in the closed position.

35. A humidifier according to claim 34, wherein the plurality of heat stakes comprises six heat stakes.

36. A humidifier according to claim 35, wherein the plurality of heat stakes are equidistant from each other.

37. A humidifier according to claim 36, wherein the melted head portions of the heat stakes assist in holding the base plate against the tub base.

38. A humidifier according to claim 37, wherein the melted head portions are in the shape of a dome.

39. A humidifier according to claim 38, wherein the heat stakes comprise plastic.

* * * * *